United States Patent
Miyazaki et al.

(10) Patent No.: US 8,042,714 B2
(45) Date of Patent: Oct. 25, 2011

(54) REVERSE-FLOW PREVENTION PLUG FOR CONTAINER, THE CONTAINER, AND POURING DEVICE

(75) Inventors: Masayasu Miyazaki, Yokohama (JP); Manabu Ikuta, Sakai (JP)

(73) Assignee: Sumitomo Rubber Industries, Ltd., Kobe (JP)

( * ) Notice: Subject to any disclaimer, the term of this patent is extended or adjusted under 35 U.S.C. 154(b) by 1719 days.

(21) Appl. No.: 10/526,368

(22) PCT Filed: Aug. 14, 2003

(86) PCT No.: PCT/JP03/10365
§ 371 (c)(1),
(2), (4) Date: Oct. 5, 2005

(87) PCT Pub. No.: WO2004/022444
PCT Pub. Date: Mar. 18, 2004

(65) Prior Publication Data
US 2006/0065673 A1    Mar. 30, 2006

(30) Foreign Application Priority Data

Sep. 6, 2002  (JP) ................................. 2002-261891
May 15, 2003  (JP) ................................. 2003-137579

(51) Int. Cl.
*B65D 5/72* (2006.01)
(52) U.S. Cl. ........ 222/494; 222/105; 222/212; 222/213; 222/386; 222/386.5; 222/491
(58) Field of Classification Search .............. 222/94–96, 222/105, 206, 209, 212–215, 490–491, 494, 222/386.5, 386
See application file for complete search history.

(56) References Cited

U.S. PATENT DOCUMENTS

| 1,987,156 | A | * | 1/1935 | Paparello | ....................... 222/494 |
| 3,111,703 | A | * | 11/1963 | Kaufman | ....................... 401/214 |
| 3,179,300 | A | | 4/1965 | Davidson | |
| 4,342,522 | A | * | 8/1982 | Mackles | ....................... 401/214 |
| 4,846,810 | A | | 7/1989 | Gerber | |
| 5,005,732 | A | | 4/1991 | Penn | |
| 5,033,647 | A | * | 7/1991 | Smith et al. | ....................... 222/94 |
| 5,305,786 | A | * | 4/1994 | Debush | ....................... 137/512.3 |

(Continued)

FOREIGN PATENT DOCUMENTS

JP        49-97245 A    8/1974

(Continued)

*Primary Examiner* — Frederick C. Nicolas
(74) *Attorney, Agent, or Firm* — Birch, Stewart, Kolasch and Birch LLP

(57) ABSTRACT

A backflow preventing plug, a container, and a pouring device in which a container body and a plug member are provided separately in a simple shape, and tight-contact property between the plug member and a resilient member is enhanced to improve a backflow preventing function are provided.

A backflow-preventing plug includes a resilient membrane formed of a thin film for defining a flow path having an inlet port and an outlet port, and a ball-shaped plug member retained in the flow path of the resilient membrane and formed with a spherical sealing surface for restricting fluid flow by coming into tight resilient contact with a middle portion of the resilient membrane. In a container, the backflow preventing plug is attached to a container opening of a container body accommodating contents. A pouring device includes, for example, a container holder accommodating and holding the container and allowing the container body to be pressurized from the container opening side to be contractingly deformed.

23 Claims, 29 Drawing Sheets

U.S. PATENT DOCUMENTS

| | | | |
|---|---|---|---|
| 5,366,115 A | 11/1994 | Kersten et al. | |
| 5,529,213 A * | 6/1996 | Mack et al. | 222/95 |
| 5,836,484 A * | 11/1998 | Gerber | 222/494 |
| 5,887,753 A * | 3/1999 | Poolman | 222/1 |
| 5,967,377 A | 10/1999 | Glynn | |
| 6,253,967 B1 * | 7/2001 | Sperna Weiland | 222/205 |
| 6,286,725 B1 | 9/2001 | Gerber | |
| 6,325,253 B1 * | 12/2001 | Robinson | 222/212 |
| 6,357,630 B1 * | 3/2002 | Sperna Weiland | 222/207 |
| 6,396,395 B1 * | 5/2002 | Zielinski et al. | 340/425.5 |
| 6,536,631 B1 | 3/2003 | Nickels et al. | |
| 6,662,977 B2 * | 12/2003 | Gerber et al. | 222/494 |
| 7,490,744 B2 * | 2/2009 | Matsumoto et al. | 222/494 |

FOREIGN PATENT DOCUMENTS

| | | |
|---|---|---|
| JP | 144277/1972 A | 8/1974 |
| JP | 58-125466 A | 7/1983 |
| JP | 61-190447 A | 8/1986 |
| JP | 2002-002755 | 9/2002 |

* cited by examiner

"Gerber 6,286,725"

(a)

(b)

(a)

(b)

(a)

(b)

(a)

(b)

(a)

(b)

(a)

(b)

(a)

(b)

(a)

(b)

(a)

(b)

(c)

(a)

(b)

REVERSE-FLOW PREVENTION PLUG FOR CONTAINER, THE CONTAINER, AND POURING DEVICE

TECHNICAL FIELD

The present invention relates to a backflow preventing plug for a container, the container, and a pouring device for preventing outside air or the like from entering into the container for protecting contents against oxidation or bacteria.

BACKGROUND ART

Currently, food products, cosmetics, or drugs are generally manufactured with adding antioxidants or antiseptic agents for preventing oxidation or multiplication of bacteria in the products in order to maintain quality of the products as long as possible. Manufacturing products with the antioxidants or the antiseptic agents added therein is one of effective measures for increasing life of the products, enhancing value of the products, and hence contributing to industrial growth. However, in recent years, there is an increasing demand for using food products or the like in a state as natural as possible without the antioxidants or the antiseptic agents therein.

In order to restrain oxidation of the food products or multiplication of bacteria without adding the antioxidants or the antiseptic agents, measures such as manufacturing a container capable of preventing outside air from entering into the container and encapsulating the food products or the like in such a container for use may be taken. Examples of such measures in the related art are disclosed in Japanese Unexamined Patent Publication No. 2002-2755 (hereinafter referred to as Patent Document 1) and U.S. Pat. No. 6,536,631 (hereinafter referred to as Patent Document 2).

In Patent Document 1, a container "including a container body having resiliency and being formed with a discharging port at one end, an inner plug provided for closing the discharging port, an inner plug projection provided at a center of the inner plug and projecting outwardly from the discharging port, a through-hole provided in the inner plug for communicating the inside and the outside of the container body, and a nozzle member having resiliency and coming into tight contact with the peripheral edge of the discharging port and the side surface of the inner plug projection" is disclosed.

In Patent Document 2, a container having a reservoir for storing contents, and a head for discharging a predetermined amount of liquid from at least one outlet port is disclosed.

However, in the container of Patent Document 1, since the inner plug projection and the resilient nozzle member are simply in line contact with each other in the discharging direction, tight contact between the nozzle member and the inner plug projection is insufficient, and hence sufficient backflow preventing function cannot be achieved.

In the container according to Patent Document 2, since the head and the reservoir are formed integrally, the shape is complex, and hence it is difficult to manufacture.

Therefore, it is an object of the present invention to provide a backflow preventing plug for a container, the container, and a pouring device in which a container body and a plug member are separately formed in simple shapes and tight contact between the plug member and a resilient member is enhanced to improve the backflow preventing function.

DISCLOSURE OF INVENTION

In order to achieve the object described above, the present invention devises the following technical means.

Specifically, a backflow preventing plug 4 includes a thin film resilient membrane 7 defining a flow path having an intake port 9c and an outlet port 6, and a ball-shaped plug member 8 retained in the flow path in the resilient membrane 7 and formed with a spherical sealing surface 12 for restricting flow of fluid by coming into resilient contact with a middle portion of the resilient membrane 7 (See FIG. 1).

With this structure, since the plug member 8 is formed in a simple ball-shape to be held by the resilient membrane 7, the plug member 8 does not need to be integrally formed with the container body and, in addition, tight-contact between the spherical sealing surface 12 and the resilient membrane 7 allows a resilient force of the resilient membrane 7 to act on the spherical sealing surface 12, the resilient membrane 7, and respective contact points in a centripetal direction, thereby improving the backflow preventing function.

The resilient membrane 7 is formed of an elastic rubber member which is expandingly deformable in the direction away from the plug member 8 by a fluid pressure applied from the intake port 9c (See FIG. 1).

Accordingly, contents are allowed to enter between the plug member 8 and the resilient membrane 7 with releasing tight contact between the resilient membrane 7 and the plug member 8 so as to secure the flow path for the contents.

In the backflow preventing plug 4, the plug member 8 has a spherical shape (See FIG. 1).

Accordingly, the plug member 8 can be formed in a simple shape so as to facilitate manufacture and assembly of the backflow preventing plug 4.

In the backflow preventing plug 4, the plug member 8 has an ellipsoidal shape (See FIG. 7).

Accordingly, the plug member 8 can be formed into a simple shape so as to facilitate manufacture and assembly of the backflow preventing plug 4.

In the backflow preventing plug 4, the outlet port 6 of the resilient membrane 7 has a slit-shape (See FIG. 4).

Accordingly, outflow of contents from the outlet port 6 can be adequately stopped when discharge of contents is stopped.

The resilient membrane 7 is formed with an annular projection 15 capable of coming into tight contact with the plug member 8 on the inner surface thereof (See FIG. 1).

Accordingly, the backflow preventing plug 4 is provided with a double-sealing structure comprising a tight contact between the film portion of the resilient membrane 7 and the spherical sealing surface 12 of the plug member 8 and another tight contact between the annular projection and the plug member 8, whereby further enhanced sealing is achieved.

The backflow preventing plug 4 includes discharge guiding means for guiding contents, which have passed through the flow path formed by the expansion of the resilient membrane 7 due to an increase in fluid pressure on the intake port 9c side, toward the outlet port 6 (See FIG. 1).

Accordingly, the contents can be reliably discharged from the outlet port 6.

The backflow preventing plug 4 further includes a clearance forming projection 13 for forming a clearance for guiding flow of fluid contents to the outlet port 6 by positioning the plug member 8 with respect to the outlet port 6 (See FIG. 1).

The clearance forming projection 13 provides a space between the outlet port 6 and the plug member 8 to prevent the plug member 8 from closing the outlet port 6, so that the contents can be reliably discharged from the outlet port 6.

There is further provided separating means for separating the outlet port 6 of the resilient membrane 7 from the plug member 8 for preventing tight contact therebetween when contents are discharged from the outlet port 6 (See FIG. 7).

Accordingly the backflow preventing plug 4 can reliably discharge the contents.

In a container 1, the backflow preventing plug 4 is attached to a container opening 2 of a container body 3 in which contents are accommodated (see FIG. 1).

With this structure, since the plug member 8 is formed in a simple ball-shape to be held by the resilient membrane 7, the plug member 8 does not need to be integrally formed with the container body 3 and, in addition, tight-contact between the spherical sealing surface 12 and the resilient membrane 7 allows a resilient force of the resilient membrane 7 acts on the spherical sealing surface 12, the resilient membrane 7, and respective contact points in a centripetal direction, thereby improving the backflow preventing function.

The container 1 includes fixed quantity discharging means 50 for allowing contents to be discharged by a fixed quantity (see FIG. 8, FIG. 11).

With this arrangement, a fixed quantity of contents can be conveniently discharged every time when using the container 1.

The container body 3 is formed in a bag shape which is contractively deformable for discharging contents from the container opening 2 (See FIG. 19).

With this structure, the contents can be discharged from the outlet port 6 of the backflow preventing plug 4 by contractingly deforming the container body 3.

The container body 3 is formed in an accordion shape which is contractively deformable for discharging contents from the container opening 2 (See FIG. 21).

With this structure, by causing the container body 3 to contractingly deform in a folding manner, the contents can be discharged from the outlet port 6 of the backflow preventing plug 4.

The container body 3 includes a cylindrical member 51 for accommodating contents and a piston 52 axially slidably fitted into the cylindrical member 51 (See FIG. 25).

Accordingly, the contents can be discharged from the outlet port 6 of the backflow preventing plug 4 by sliding the piston 52.

A pouring device 43 includes an outer mantle 42 which surrounds the container body 3 of the container 1 with an intermediary of a space, and is resiliently deformable, so that the container body 3 can be contractingly deformed through air in the space by a resilient deformation of the outer mantle due to an external pressure (See FIG. 22).

With this structure, since the outer mantle 42 causes the container body 3 to contract by its resilient deformation and, thereafter, is restored to the original shape when the resilient deformation is released, the outer mantle 42 can contract the container body 3 always under the same condition even when the container body 3 is under contractingly deformed condition.

The pouring device 43 includes a container holder 47 for holding the container 1 and allowing the container body 3 to be pressurized from the container opening 2 side for contracting deformation (See FIG. 23).

With this arrangement, the container 1 can be used in a stabled posture.

The pouring device 43 includes a cartridge holder 66 for supporting the container 1, and a fixed quantity discharging mechanism 67 for causing contents to be poured by a predetermined small amount at every pushing operation for discharging the contents from the container opening 2 of the container 1 (See FIG. 26).

Accordingly, the pouring device 43 can pour the contents by a fixed quantity every time when used.

The pouring device 43 further includes a pushing member 56 for pushing the piston 52 with respect to the cylindrical member in the content discharging direction (See FIG. 25).

Accordingly, the pouring device 43 can pour contents easily by moving the pushing member 56.

BEST MODE FOR CARRYING OUT THE INVENTION

Figures 1A, 1B, 1C:
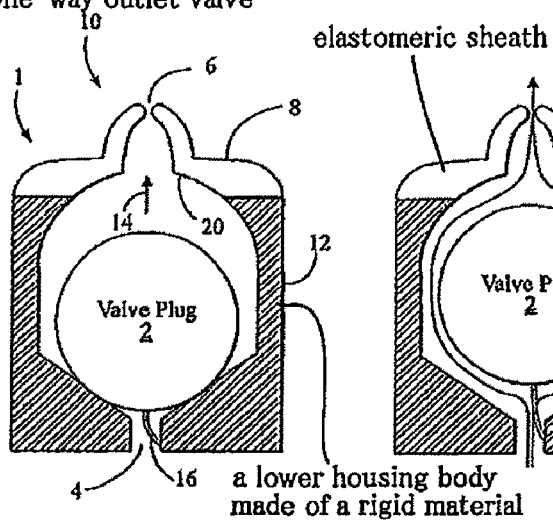
FIG. 1 is a vertical cross-sectional view of a container and a backflow preventing plug showing a first embodiment of the present invention.

Embodiments of the present invention will now be described with reference to the drawings.

A container 1 according to the present invention is used for preventing backflow (entering) of air therein and restraining oxidation or multiplication of bacteria in contents in the container. The container 1 can accommodate various objects including fluid contents in a state of gas, liquid, paste, for example, food products such as mayonnaise, ketchup, sauce, grated horse-radish, cosmetics in a state of cream, and medical products such as ointment, or eye lotion.

FIGS. 1 to 4 show a first embodiment of the present invention. The container 1 includes a container body 3 having a container opening 2 at one end thereof, and a backflow preventing plug 4 provided on the container opening 2. The container opening 2 is formed with a discharge port 5, and contents discharged from the discharge port 5 are passed through a flow path in a resilient membrane 7 and discharged from an outlet port 6.

The container 3 is formed of a resin material such as polyethylene, polypropylene, PET, nylon, TPE, or the like, and a side surface thereof has flexibility, so that contents are discharged from the discharge port 5 when its side surface is pushed by fingers or the like.

The backflow preventing plug 4 includes the resilient membrane 7 provided on the container opening 2 and formed with the outlet port 6, and a plug member 8 disposed in the resilient membrane 7 and capable of blocking flow of contents between the container opening 2 and the outlet port 6.

The resilient membrane 7 is formed of a thin film in a sack shape (bag shape) having a distal end 9a formed in a substantially semispherical shape, a body portion (middle portion) 9b in a cylindrical shape, a proximal end defining an opening 9c as an intake port (9c) for contents, and a circular flange 11 formed on the outer peripheral edge of the opening 9c. The resilient membrane 7 is attached to the container opening 2 so as to cover the discharge port 5 of the container body 3.

The distal end 9a of the resilient membrane 7 is formed with the outlet port 6 for contents, and the outlet port 6 and the discharge port 5 are placed apart from each other in the discharging direction of contents. The contents discharged form the discharge port are passed through the flow path in the body portion 9b of the resilient membrane 7 and, then, discharged from the outlet port 6.

The resilient membrane 7 is formed of any material selected from rubber, resin or the like in view of physical properties such as viscosity or grain size, chemical properties such as PH, appearance, economical conditions, usability or the like of contents.

For example, an elastic rubber member formed at least one of NR, SBR, BR, NBR, CR, EPM, EPDM, IR, IIR, FKM, VMQ, U, T, CO, ACM and the like, SBS, SIBS, SEBS, SIS, SEPS, SEEPS, TPO, TPU, TPEE, TPAE, TPVC, 1, 2-polybutadien thermoplastic elastomer, fluorinated thermoplastic elastomer, and combinations thereof may be used.

The outlet port 6 of the resilient member 7 is formed in a slit shape of a straight line (may be a cross-shape), or is formed in a duckbill shape, and the edges thereof are in tight contact with each other. With the outlet port 6 formed in the slit-shape in this manner, contents are discharged by pressingly opening the outlet port 6 when the side surface of the container body 3 is pressed, while the outlet port 6 is closed so as to stop the flow of contents instantaneously by its resilient restoring force when pushing operation is stopped. With this structure, since the outlet port 6 is closed instantaneously, contents are prevented from staying around the peripheral edge of the outlet port 6, and can be stopped completely. Therefore, although the outlet port 6 may be formed in an opening of a circular shape, for example, in plan view, it is more preferable to form it in a slit-shape or in a duckbill shape in view of the instantaneously stopping property.

The plug member 8 is disposed in the body portion 9b of the resilient membrane 7 and comprises a solid spherical body formed of, for example, hard resin or the like. The plug member 8 is forcedly inserted into the resilient membrane 7 through the opening 9c and disposed inside of the distal end 9a and the body portion 9b.

The plug member 8 has a diameter larger than an inner diameter of the body portion 9b of the resilient membrane 7. Therefore, when the plug member 8 is provided in the body portion 9b of the resilient membrane 7, the plug member 8 comes into tight contact with an inner surface of the resilient membrane 7, and the body portion 9b of the resilient membrane 7 which comes into contact with the plug member 8 is resiliently deformed so as to expand outwardly. The plug member 8 is held by the resilient force generated by resilient deformation of the resilient membrane 7, thereby being retained within the resilient membrane 7.

Since the plug member 8 has a spherical shape, the surface thereof forms a spherical surface. The plug member 8 performs sealing function by means of resilient and tight contact with the resilient membrane 7. Hereinafter, the surface (spherical surface) of the plug member 8 performing sealing function is referred to as a spherical sealing surface 12. Since the spherical sealing surface 12 has a spherical surface shape, a larger sealing area than a flat surface can be secured.

Since the resilient membrane 7 is formed of a thin film, the inner surface and the outer surface of the resilient membrane 7 are resiliently deformed into a spherical shape corresponding to the spherical shape of the spherical sealing surface 12 at the tight-contact portion. Therefore, sealing between the spherical sealing surface 12 and the resilient membrane 7 in the tight-contact portion is performed by tight contact between the spherical surfaces. In this manner, with the tight contact between spherical surfaces, the resilient force of the resilient membrane 7 at each contact point in the tight-contact area acts in the centripetal direction directed toward the center of the sphere of the spherical sealing surface 12. In other words, since a uniform resilient force (resilient restoring force) in the centripetal direction acts at any contact points, tight contact property is improved, and thus a reliable and high backflow preventing function can be achieved over a large area.

The resilient membrane 7 is provided with a projection (clearance forming projection) for locking and positioning the plug member 8 on an inner surface of the distal end 9a at a position near the outlet port 6, and the projection serves as clearance forming means 13 for forming a clearance between the outlet port 6 and the plug member 8. A plurality of projections are provided as the clearance forming means 13 at positions apart from each other in the circumferential direction on the inner surface of the resilient membrane 7. In the first embodiment, four projections are provided as the clearance forming means 13. The clearance forming means 13 in the shape of projection is positioned apart from the outlet port 6 in the content discharging direction. Therefore, the plug member 8 locked by the clearance forming means 13 in the shape of the projection is positioned apart from the outlet port 6 so that a clearance 14 is formed between the plug member 8 and the outlet port 6.

With thus formed clearance 14, the plug member 8 is prevented from coming into tight contact with the outlet port 6 and closing the same, so that contents can be advantageously discharged with releasing the sealing state with a desired pressure. In other words, with the clearance 14 formed by the projection on the resilient membrane 7, the plug member 8 is prevented from coming into tight contact with the outlet port 6 and closing the same, so that contents entering from the intake port 9c and flowing through the flow path can be guided reliably to the outlet port 6. Therefore, the resilient membrane 7 is provided with discharge guiding means for guiding contents passed through the flow path to the outlet port 6. The discharge guiding means is provided closer to the distal end 9a of the resilient membrane 7.

The body portion 9b of the resilient membrane 7 is provided with an annular projection 15 (seal ring portion) for coming into contact with the plug member 8 and performing sealing function on the inner surface thereof in addition to the sealing performed by tight contact between the spherical sealing surface 12 and the resilient membrane 7. The annular projection 15 is provided at a position apart from the outlet port 6, and when the plug member 8 is provided in the resilient membrane 7, the plug member 8 is clamped between the projecting clearance forming means 13 and the annular projection 15. In other words, the projecting clearance forming means 13 and the annular projection 15 restrict movements of the plug member 8 and, further, the annular projection 15 supports the plug member 8 so as not to move toward the container opening 2. Therefore, the container 1 having the backflow preventing plug 4 has a double-sealing structure in which sealing is performed at two positions of the tight contact portion between the spherical sealing surface 12 and the resilient membrane 7, and the contact portion between the plug member 8 (spherical sealing surface 12) and the annular projection 15. With such a double-sealing structure, reliable and sufficient backflow preventing function can be achieved. Alternatively, since the spherical sealing surface 12 and the resilient membrane 7 are brought into tight contact with each other and the reliable and sufficient backflow preventing function can be achieved even only with such tight contact, it is also possible to employ a structure in which the annular projection 15 serves only to support the plug member 8. In this case, for example, the annular projection 15 may be constituted of a plurality of projections disposed in a ring shape.

Figure 2:
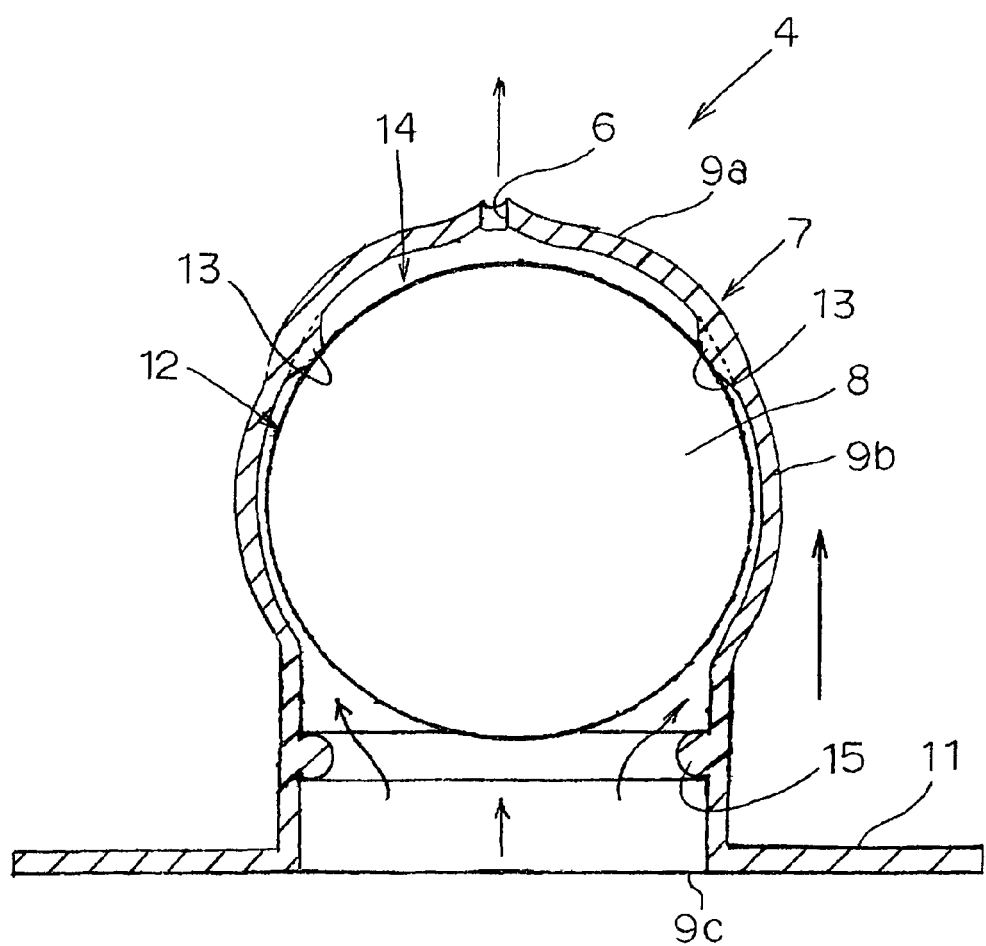
FIG. 2 is a vertical cross-sectional view of the container and the backflow preventing plug showing a state in which contents are discharged.
Figure 3:
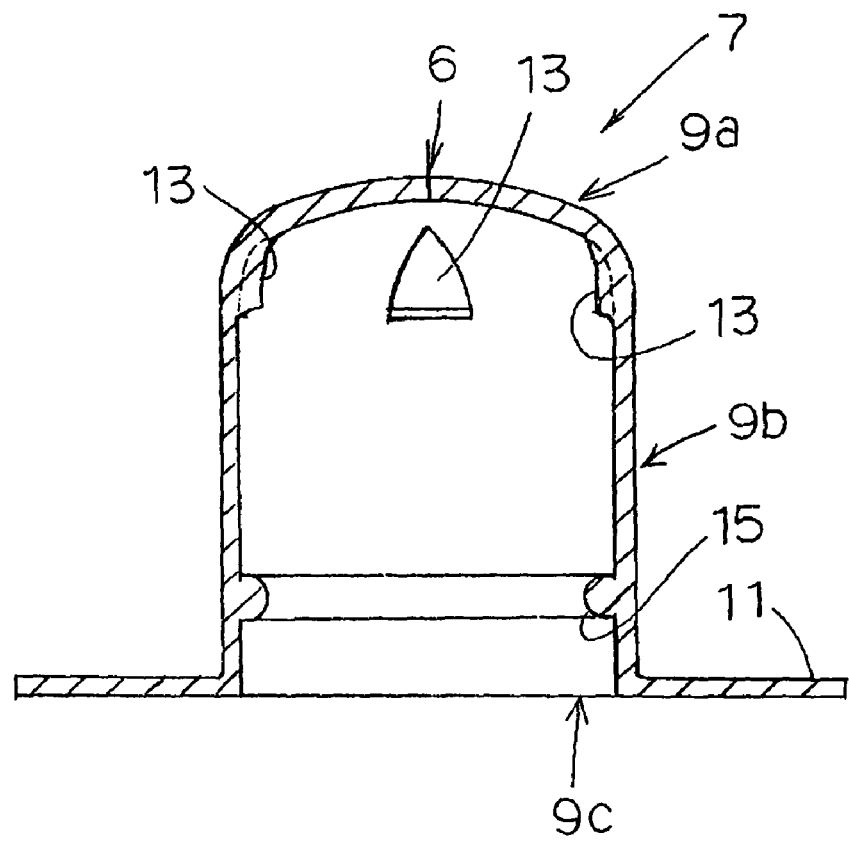
FIG. 3 is a vertical cross-sectional view of a resilient membrane.
Figure 4:
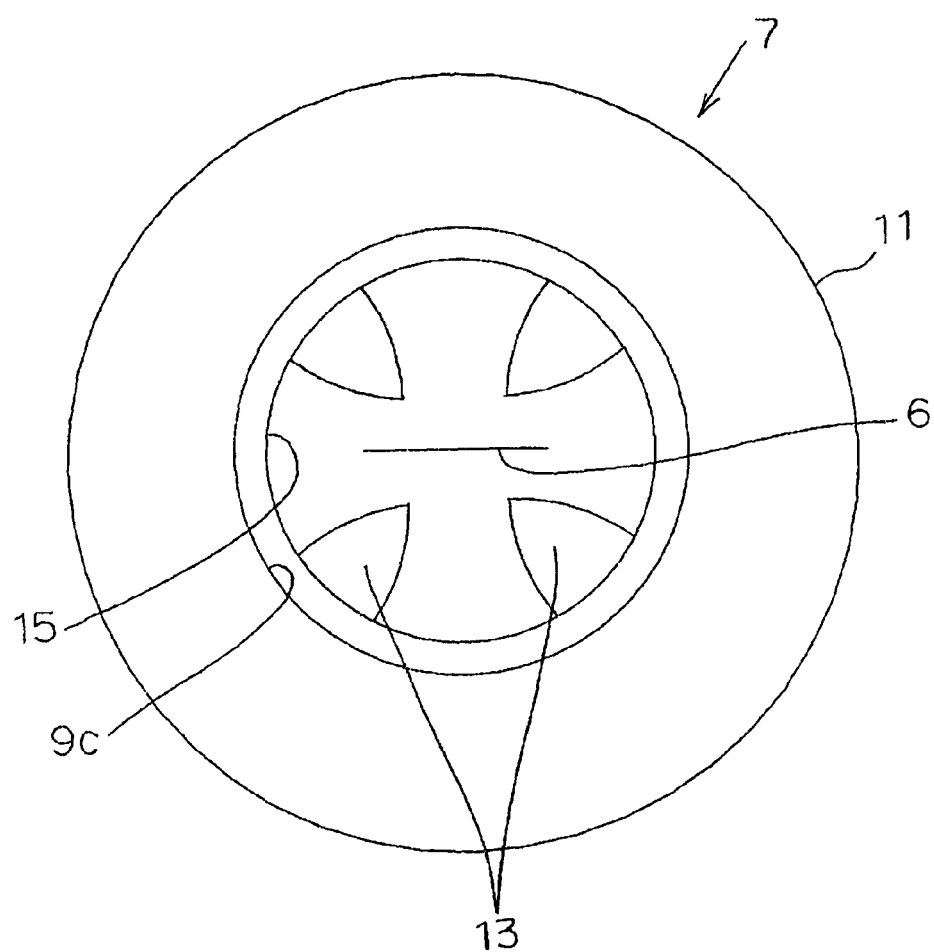
FIG. 4 is a bottom view of the resilient membrane.

In FIG. 2, when using the container 1, contents are discharged from the discharge port 5 by pushing the side surface of the container body 3 with fingers or the like. Subsequently, the contents discharged from the discharge port 5 exert a pressure on the plug member 8, whereby the resilient membrane 7 receives pressure and hence is resiliently deformed so as to be extended in the discharging direction. At this time, the plug member 8 moves (transferred) in the discharging direction with respect to the container body 3 with resiliently deforming the resilient membrane 7 as described above. When the resilient membrane 7 is resiliently deformed in this manner, the plug member 8 is moved away from the annular projection 15 and hence sealing between the plug member 8 and the annular projection 15 is released. Following this release, the contents move over the annular projection 15 and flow into the sealed portion (the tight contact portion) between the spherical sealing surface 12 and the resilient membrane 7. The contents push the resilient membrane 7 in the tight-contact state so as to resiliently and expansively deform the resilient membrane 7 outward, thereby releasing the sealed portion between the spherical sealing surface 12 and the resilient membrane 7, and entering into the clearance 14 on the side of the outlet port 6. The clearance 14 is finally filled with the contents, and the contents press the discharging port 6 in the discharging direction to be discharged toward the outside.

Then, when the pushing on the side surface of the container body 3 is stopped, the resilient membrane 7 resiliently deformed by the contents comes again into contact with the spherical sealing surface 12 of the plug member 8 by its resilient restoring force, and the sealed state is restored.

A male screw 16 is formed on a side surface of the container opening 2, and a cap 18 having a female screw 17 thereon is fitted on the male screw 16. A shoulder 18a for fixing the resilient membrane 7 is formed on a side portion of the cap 18. The flange 11 of the resilient membrane 7 is clamped between the shoulder 18a and a front surface 19 of the container opening 2, and when the cap 18 is rotated to the screw-tightening direction, the flange 11 is pressed by the shoulder 18a so that the resilient membrane 7 is fixed to the container opening 2. It is also possible to fix the resilient membrane 7 to the container opening 2 by adhering with adhesive agent or the like or welding between the flange 11 of the resilient membrane 7 and the front surface 19 of the container opening 2.

A lid 21 is provided on the front surface side of the cap 18 via a hinged portion 20 provided on the peripheral edge of the front surface so as to be capable of opening and closing. Such a cap 18 can be opened and closed easily by a one-touch operation for use.

The fitting portion between the female screw 17 of the cap 18 and the male screw 16 on the side surface of the container opening 2 is preferably welded, so that the fitting portion can be prevented from loosening and hermeticity of the container 1 can be secured. It is also possible to provide a mechanism for preventing a reverse rotation of the cap 18, such as a ratchet mechanism, at this fitting portion.

An outer side surface of the cap 18 is formed with a notch 22 extending along a circumferential direction thereof. Where the fitting portion is welded, the cap 18 is formed to be cut into tow pieces along this notch 22 to remove the backflow preventing plug 4. With this structure, when the contents cannot be easily discharged by pressing the container body 3 due to, for example, decrease in remaining amount of contents, the backflow preventing plug 4 can be removed so that the contents can be discharged easily without pressing the side surface of the container body 3 with a strong force, whereby even a decreased amount of contents can advantageously be used up.

In the tight contact portion between the plug member 8 and the resilient membrane 7, the diameter a of the outer surface of the resilient membrane 7 in a lateral direction at an outermost position in a resiliently deformed area thereof is substantially the same as the inner diameter (aperture diameter) b of the discharge port 5 or slightly larger than the inner diameter b, so that the plug 4 removed for using up the contents as described above can be fitted into the discharge port 5 from the distal end thereof for closing the same.

Figure 5:
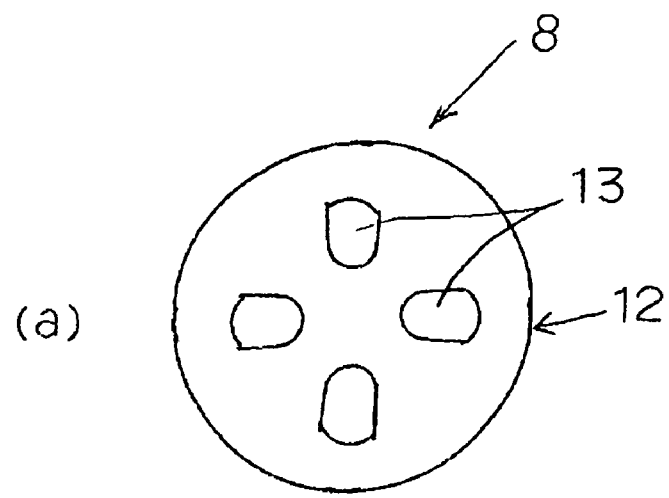
FIG. 5 shows a second embodiment of the present invention, in which (a) is a plan view of a plug member, and (b) is a side view of the plug member.
Figure 5:
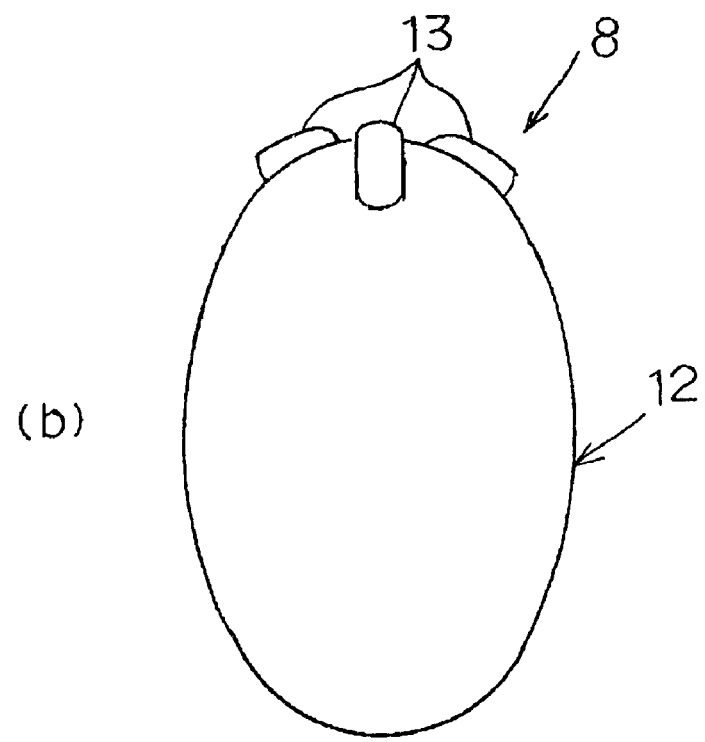

In a second embodiment shown in FIG. 5, the plug member 8 is formed in a substantially oval shape in side view. At one end of the plug member 8 in the longitudinal direction, the projection (clearance forming projection) 13 is formed for forming a clearance between the outlet port 6 and the plug member 8 in the resilient membrane 7, which serves as the clearance forming means 13. In this case, it is not necessary to form the clearance forming means 13 on the resilient membrane 7 as in the first embodiment. A plurality of clearance forming means 13 are provided at an interval in a lateral circumferential direction of the plug member 8, and in the figures, four clearance forming means are provided. The spherical sealing surface 12 is formed on a middle portion in the longitudinal direction of the plug member 8. Other points are the same as the structure of the first embodiment, and hence the same effects can be obtained.

Figure 6:
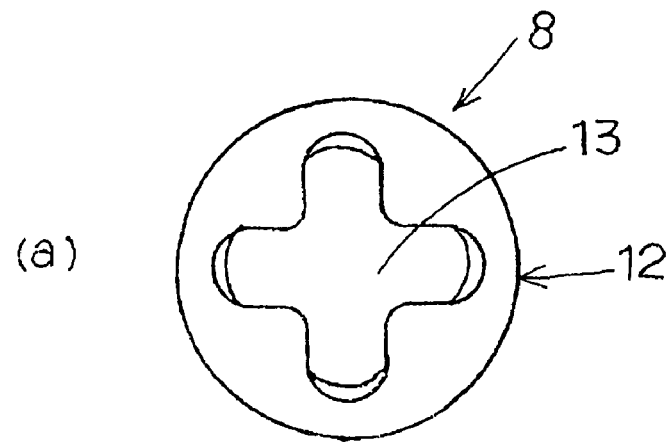
FIG. 6 shows a third embodiment of the present invention, in which (a) is a plan view of the plug member, and (b) is a side view of the plug member.
Figure 6:
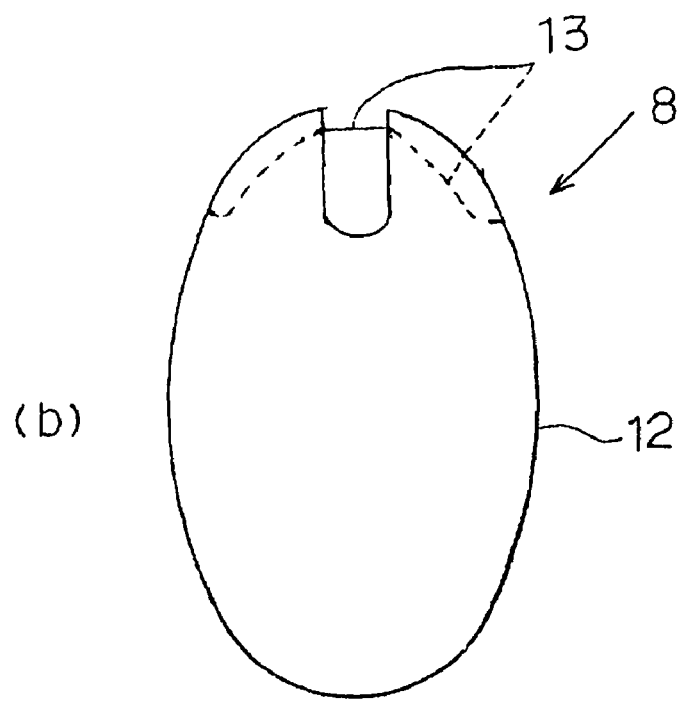

A third embodiment shown in FIG. 6 is different from the second embodiment in that a recess for forming a clearance between the outlet port 6 and the plug member 8 is provided on the plug member 8 in the resilient membrane 7 instead of the projecting clearance forming means 13 provided on the plug member 8 in the second embodiment, and serves as the clearance forming means 13. Other points are the same as the structure in the second embodiment, and the same effects can be obtained.

Figure 7:
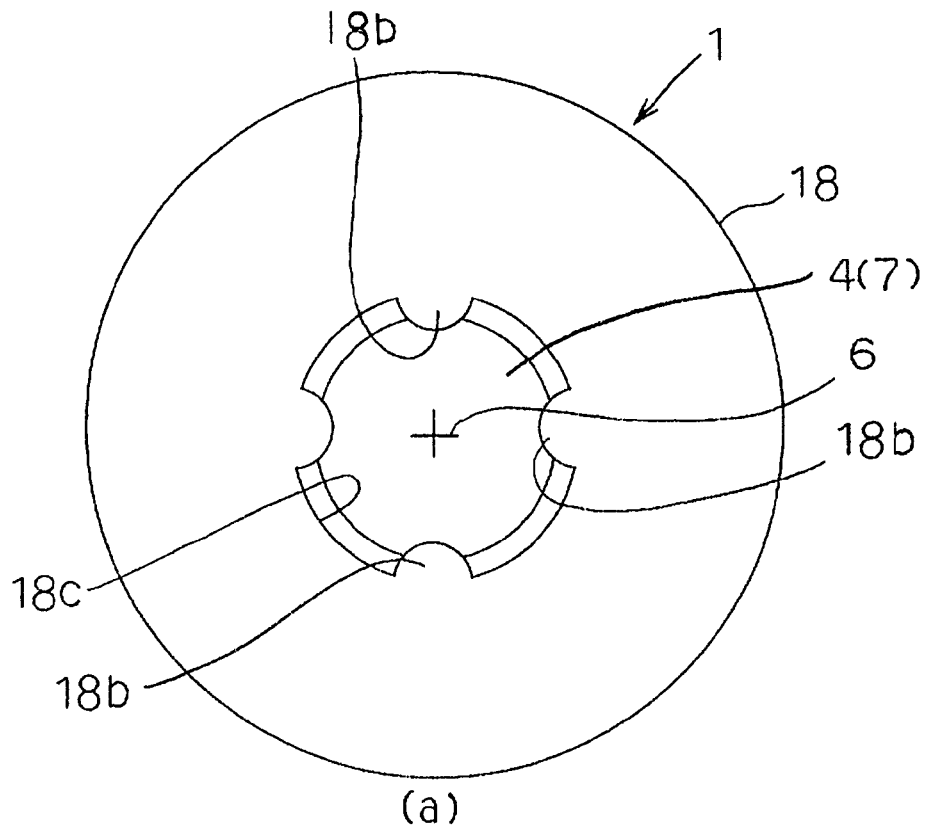
FIG. 7 shows a backflow preventing plug and a container according to a fourth embodiment, in which (a) is a plan view, and (b) is a vertical cross-sectional view.
Figure 7:
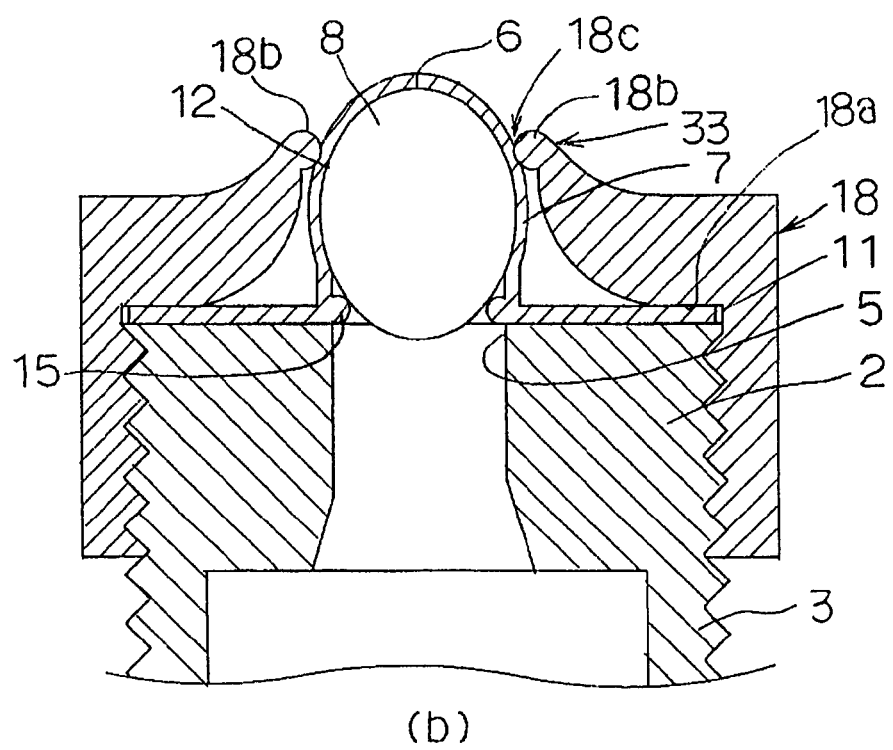

In a fourth embodiment shown in FIG. 7, the shape of the resilient membrane 7, the shape of the plug member 8, the structure of the cap or the like are partly different from the first embodiment.

Specifically, the resilient membrane 7 does not have the clearance forming means 13 in the first embodiment (FIG. 1). While the plug member 8 was described to have a spherical shape in the first embodiment, the one having an oval shape (oval shape in side view, egg-shape) is used in the fourth embodiment. A projection 18b which abuts against the resilient membrane 7 is formed on a distal end surface of the cap 18. The projection 18b abuts against the resilient membrane 7 at a portion above a position where the lateral width of the plug member 8 is the maximum. Four projections 18b are formed along a periphery of an edge of a hole 18c formed substantially at the center of the distal end surface of the cap 18. The number of the projections 18b may be one to three or five or more. Other parts of the structure are the same as the container 1 and the backflow preventing plug 4 of the first embodiment.

According to the container 1 and the backflow preventing plug 4 in the fourth embodiment, when the container body 3 is pressed from outside for discharging contents, the contents flow toward the distal end of the resilient membrane 7 with pushing the resilient membrane 7 outward so as to release tight contact between the resilient membrane 7 and the spherical sealing surface 12 of the plug member 8 while pressing the plug member 8 in the discharging direction, and are discharged from the discharge port at the distal end of the resilient membrane 7.

In this case, the plug member 8 is pushed by the contents first, and then moved toward the discharging direction, whereby the resilient membrane 7 is expanded in the discharging direction as a whole. At this time, the projection 18b of the cap 18 being in abutment with the outer surface of the resilient membrane 7 restricts the movement of the plug member 8 through the abutting portion with respect to the resilient membrane 7. In other words, the container 1 is provided with restricting means 33 for restricting deformation of the backflow preventing plug 4 or movement of the plug member 8 when the contents are discharged from the backflow preventing plug 4. The restricting means 33 is provided for securing the flow path for the contents between the plug member 8 and the resilient membrane 7 by restricting the movement of the plug member 8 so as to prevent the outlet port 6 and the plug member 8 from coming into tight contact with each other and obstructing discharge of the contents when the contents presses the plug member 8.

In other words, since the backflow preventing plug 4 includes the cap 18 as a component and the outlet port 6 and the plug member 8 are separated by the projection 18b of the cap 18 when the contents are discharged from the outlet port 6, the backflow preventing plug 4 is provided with separating means for separating the outlet port 6 and the plug member 8 so as not to be brought into tight contact with each other when the contents are discharged from the outlet port 6. With the separating means, the plug member 8 is prevented from coming into tight contact with and hence closing the outlet port 6 when the contents are discharged from the outlet port 6, so that the contents can reliably discharged.

The projection 18b and the resilient membrane 7 do not need to be configured to abut with each other, that is, they may be disposed apart from each other and arranged to come into abutment with each other by an expansion of the resilient membrane 7 for discharging contents. In such a structure as well, the projection 18b restricts the movement of the plug member 8 through the resilient membrane 7 to secure the flow path for the contents.

Figure 8:
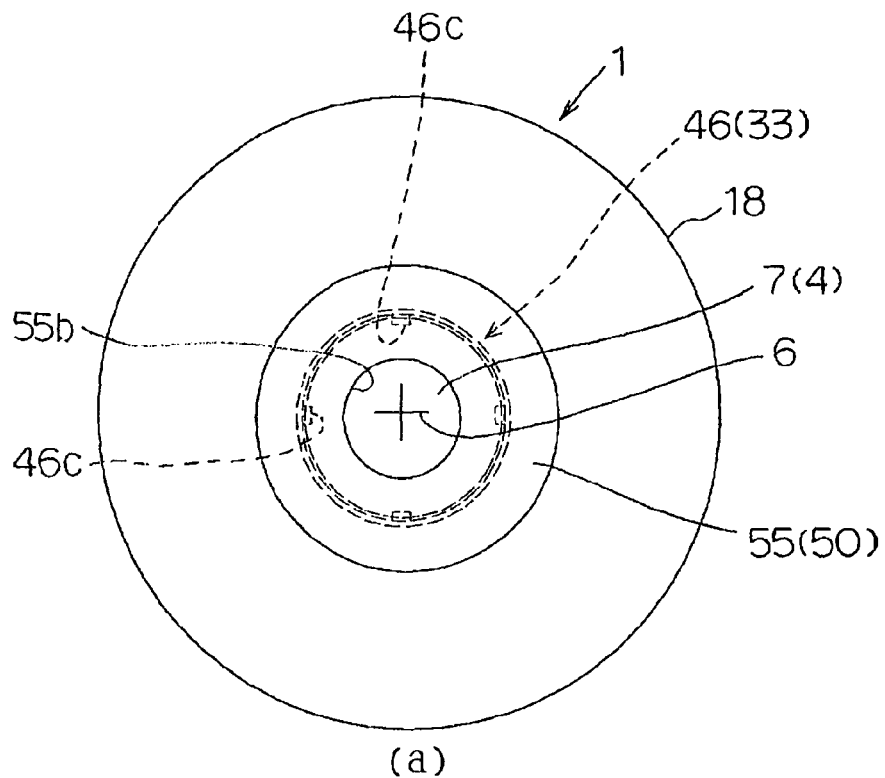
FIG. 8 shows a backflow preventing plug and a container according to a fifth embodiment, in which (a) is a plan view, and (b) is a vertical cross-sectional view.
Figure 8:
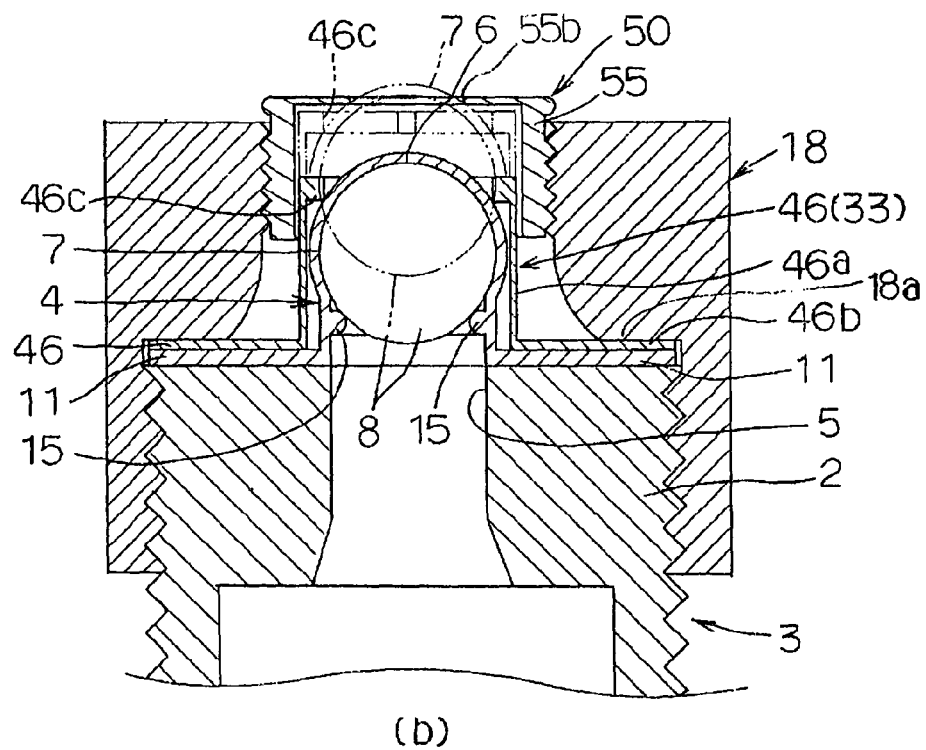
Figure 9:
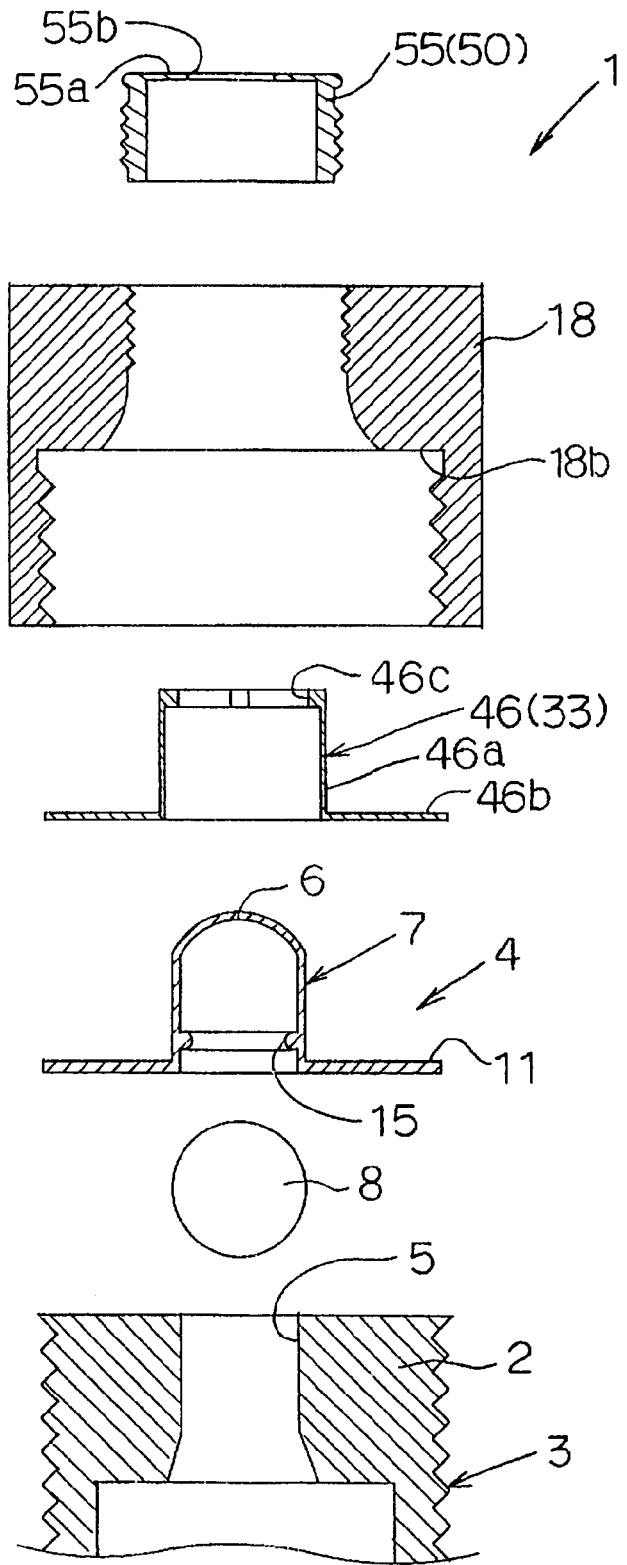
FIG. 9 is an exploded vertical cross-sectional view of the backflow preventing plug and the container of the above embodiment.
Figure 10:
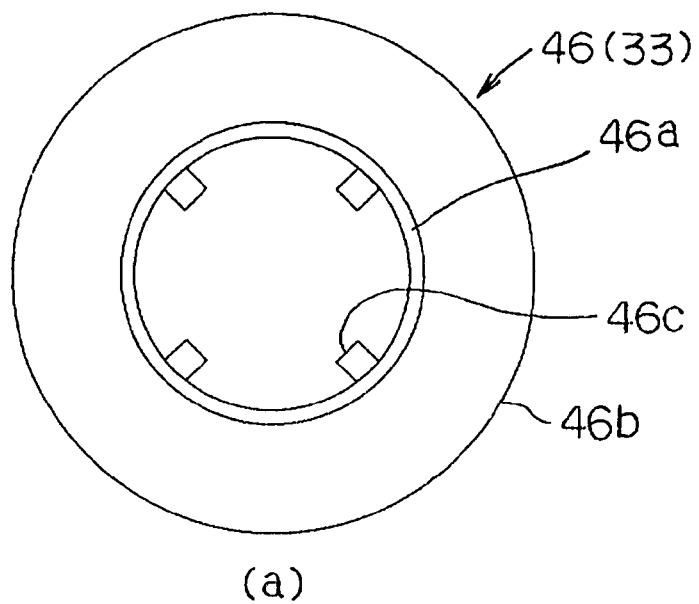
FIG. 10 shows a restricting member of the above embodiment, in which (a) is a plan view, and (b) is a perspective view.
Figure 10:
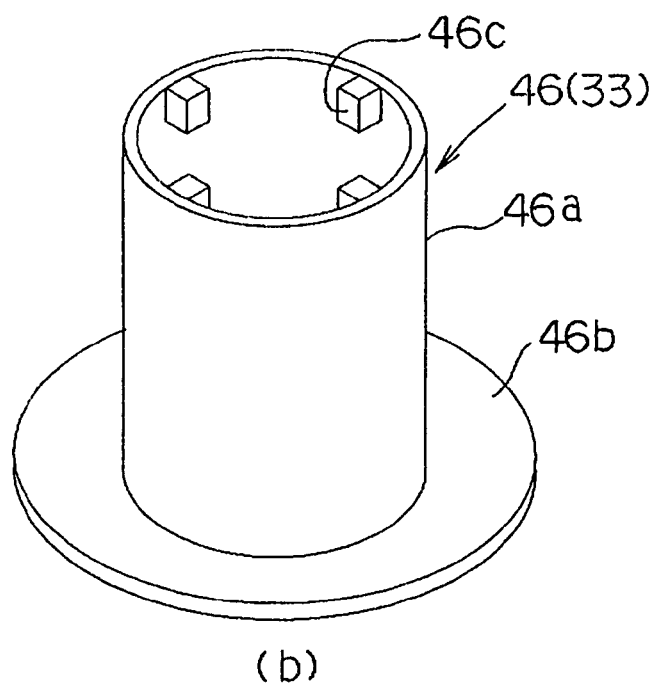

In the container 1 in a fifth embodiment shown in FIG. 8 to FIG. 10, the relation between the plug member 8 and the resilient membrane 7 is the same as the fourth embodiment shown in FIG. 7. Specifically, the resilient membrane 7 does not have the clearance forming means 13, while the annular projection 15 is formed on the inner surface at the middle portion in the longitudinal direction of the body portion 9b of the resilient membrane 7. The container 1 includes restricting means 33 for restricting deformation of the backflow preventing plug 4 or movement of the plug member 8 when contents are discharged from the backflow preventing plug 4. The restricting means 33 includes a restricting member 46 which is attached to the container opening 2 so as to cover the backflow preventing plug 4. The restricting member 46 is formed of elastic resilient member. For example, an elastic rubber or a resilient resin material is preferably employed.

As shown in FIG. 10, the restricting member 46 includes a cylindrical portion 46a through which the body portion of the plug member 8 is inserted, and a flange 46b formed on one end of the cylindrical portion 46a in the axial direction. The other end of the cylindrical portion 46a in the axial direction has an opening and is formed with a projection 46c projecting radially inwardly of the cylindrical portion 46a on an inner side (inner surface) thereof.

The flange 46b of the restricting member 46 and the flange 11 of the resilient membrane 7 are overlapped with each other, and outer peripheral portions of the respective flanges 11, 46b are pressed against the front surface of the container opening 2 and fixed thereto by the shoulder 18a of the cap 18.

The cap 18 is provided on a mouth portion at a distal end thereof with fixed quantity discharging means 50 for discharging contents by a fixed quantity every time when the container 1 is used. The fixed quantity discharging means 50 includes a cylindrical member 55 attached to the mouth portion on the distal end of the cap 18. The cap 18 is formed with a female screw on the inner surface on the distal end thereof, and an outer surface of the cylindrical member 55 is formed with a male screw to be engaged with the female screw.

The cylindrical member 55 is formed with a front wall 55a projecting radially inwardly of the cylindrical member 55 on one end in a longitudinal direction thereof. The front wall 55a is formed in a ring-shape on one end of the cylindrical member 55 in the longitudinal direction. At the center of the front wall 55a in front view is formed with a circular hole 55b.

In the container 1 constructed as described above, when the side surface of the container body 3 is pressed to cause contents to be discharged, the contents discharged from the discharge port 5 of the container opening 2 enter into between the resilient membrane 7 and the plug member 8 so as to separate the resilient membrane 7 being in tight contact with the plug member 8 while pressing the plug member 8 in the discharging direction. At this time, the plug member 8 pressed by the contents moves in the discharging direction to cause the resilient membrane 7 to be resiliently deformed so as to be expanded in the discharging direction.

Then, the outer surface of the resilient membrane 7 comes into abutment with the projection 46c of the restricting member 46, whereby the projection 46c comes into abutment with the outer surface of the resilient membrane 7 to restrict the movement of the plug member 8 as in the case of the fourth embodiment described above. Therefore, contents pass between the resilient membrane 7 and the plug member 8 with separating the resilient membrane 7 and the plug member 8 in tight contact with each other, and are discharged from the outlet port 6.

When the contents are discharged in this manner, the restricting member 46 is pressed by the resilient membrane 7 to be resiliently deformed in the discharging direction as shown by the alternate long and two short dashes in FIG. 8 in a state in which the projection 46c is kept in abutment with the outer surface of the resilient membrane 7.

On the other hand, the resilient membrane 7 expands in the discharging direction together with the restricting member 46 as shown by the alternate long and two short dashes in FIG. 8 while discharging the contents.

The resilient membrane 7 and the restricting member 46 expand in the discharging direction until the resilient membrane 7 comes into abutment with the front wall 55a of the cylindrical member 55. When the resilient membrane 7 abuts against the front wall 55a, the front wall 55a holds the outer periphery of the resilient membrane 7 and performs sealing with respect to the plug member 8, whereby the flow path for the contents in the backflow preventing plug 4 is blocked, and discharge is forcedly terminated.

In this state, even if the side surface of the container body 3 is further pressed, contents are not discharged. When the pressing on the side surface of the container body 3 is released, the restricting member 46 and the resilient membrane 7 in the expanded state are contracted to the original shape by the resiliently restoring force. Then, when the side surface of the container body 3 is pressed again, the restricting member 46 and the resilient membrane 7 repeat resilient deformations (expansions) as described above, whereby the amount of discharge is limited again by the cylindrical member 55 which is an example of the fixed quantity discharging means 50. With the structure as described above, the container 1 can discharge contents by a fixed quantity every time it is used.

It is also possible to adjust the amount of discharge per use of the container 1 by changing the position of the front wall 55a by rotating the cylindrical member 55 fitted to the cap 18 in the loosening direction or in the tightening direction of the screw. In this point, it is convenient to use the backflow preventing plug 4 of the container 1 for eye lotion or the like. Therefore, in the fourth and fifth embodiments, when the container 1 is not used, since the plug member 8 and the resilient membrane 7 come into tight contact with each other, contents are not remained at the distal end of the backflow preventing plug 4.

Figure 11:
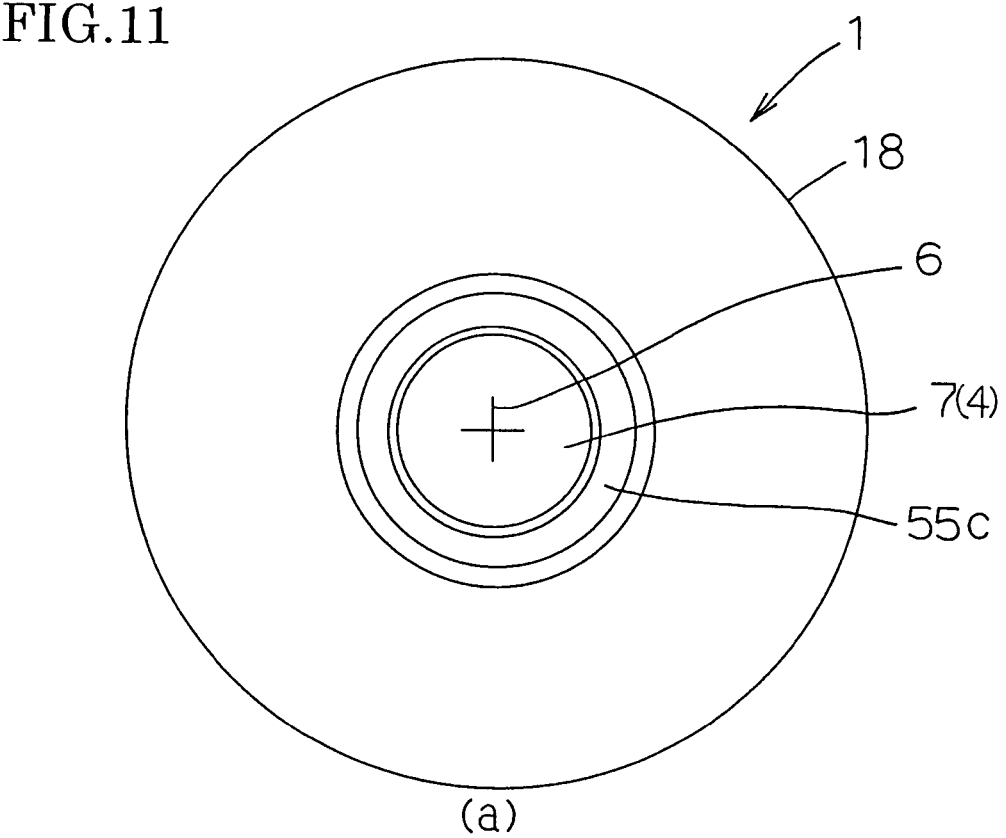
FIG. 11 shows a container and a backflow preventing plug according to a sixth embodiment, in which (a) is a plan view, and (b) is a vertical cross-sectional view.
Figure 11:
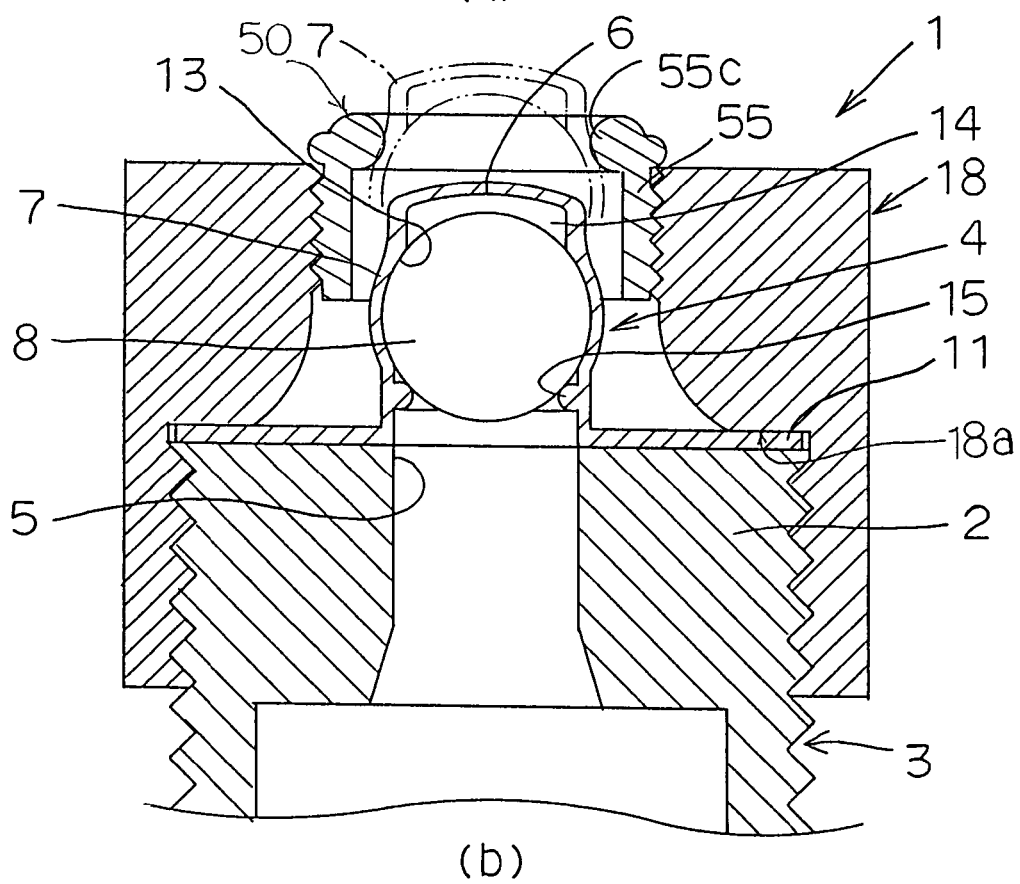

The container 1 according to a sixth embodiment in FIG. 11 includes the backflow preventing plug 4 having the clearance forming means 13 described in the first embodiment, and the fixed quantity discharging means 50 described in the fifth embodiment described above, while the restricting member 46 described in the fifth embodiment is not provided. The cylindrical member 55, which is an example of the fixed quantity discharging means 50, is formed with a radially inwardly projecting annular projection 55c on an inner surface of one end thereof. In the same manner as the front wall 55a in the fifth embodiment described above, the annular projection 55c blocks the flow path of contents by coming into abutment with the outer periphery of the resilient membrane 7 expanded by the pressure of contents to obtain sealing between the plug member 8 and the resilient membrane 7. Other parts of the structure are the same as in the container 1 in the fifth embodiment.

With such a structure as well, the container 1 can discharge a fixed quantity of the contents every time when it is used, and backflow of bacteria or outside air into the container can be prevented.

Figure 12:
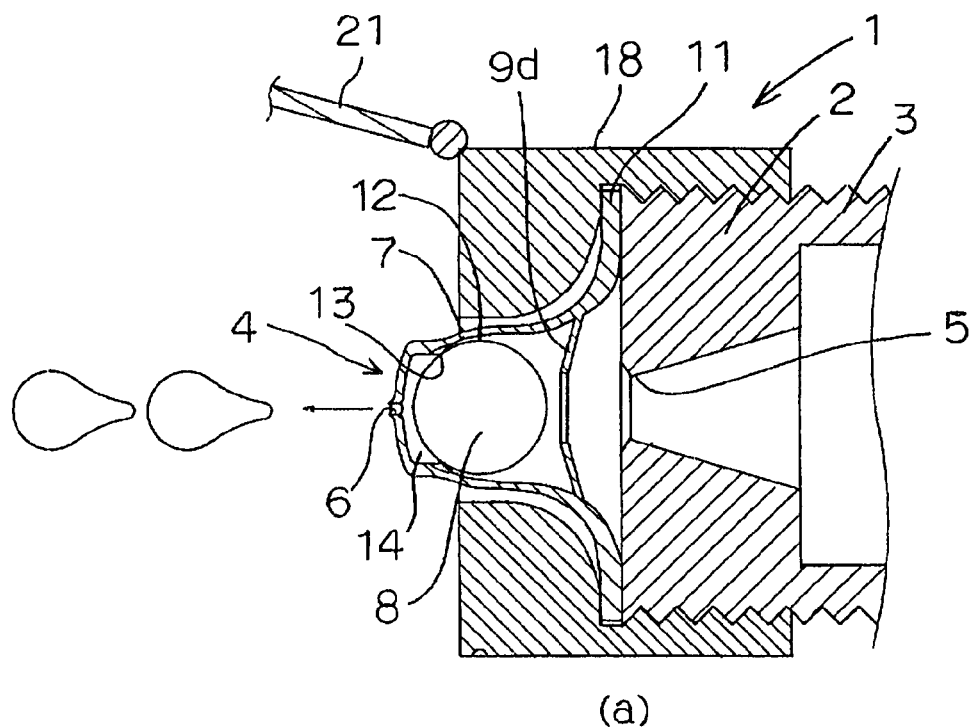
FIG. 12 shows a container and a backflow preventing plug according to a seventh embodiment, in which (a) is a vertical cross-sectional view showing a state in use, and (b) a vertical cross-sectional view showing a state not in use.
Figure 12:
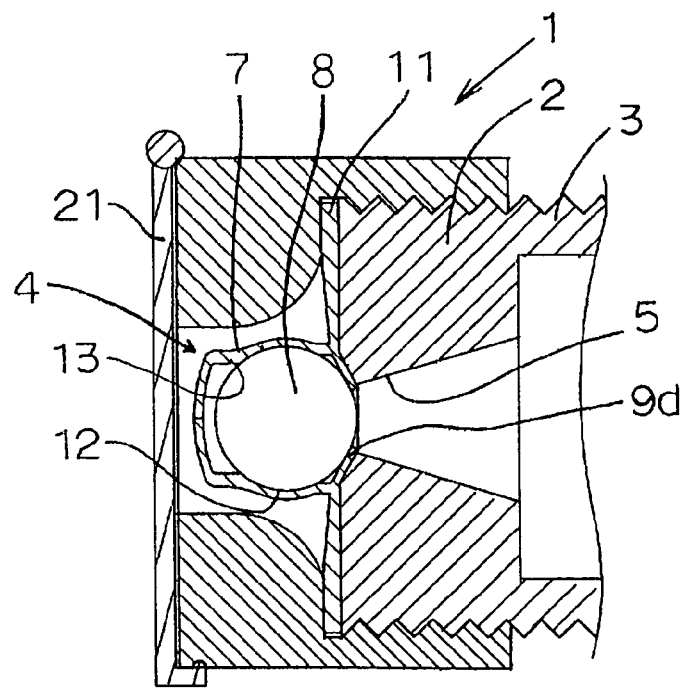

In a seventh embodiment in FIG. 12, the annular projection 15 provided on the resilient membrane 7 of the backflow preventing plug 4 has a different shape from that of the first embodiment. Specifically, in the seventh embodiment, an inner flange 9d is formed on the proximal portion of the resilient membrane 7 at a position on the inner surface corresponding to the flange 11. The inner flange 9d is formed in a plate shape extending along the peripheral edge of the opening on the proximal portion of the cylindrical portion of the resilient membrane 7 and defines a hole for passing contents therethrough at the center thereof.

As shown in FIG. 12(b), when the container 1 is not in use, the plug member 8 and the inner flange 9d come into tight contact with each other for sealing. In this state, the inner flange 9d is resiliently deformed by being pressed by the plug member 8 so as to be depressed toward the container body 3. Accordingly, sufficient tight contact between the plug member 8 and the inner flange 9d is secured and reliable sealing is achieved.

As shown in FIG. 12(a), when contents are discharged, the body portion and the flange of the resilient membrane 7 expand in the discharging direction, and the distal end (head portion) of the backflow preventing plug 4 is projected from the front surface of the cap 18 while discharging contents.

Figure 13:
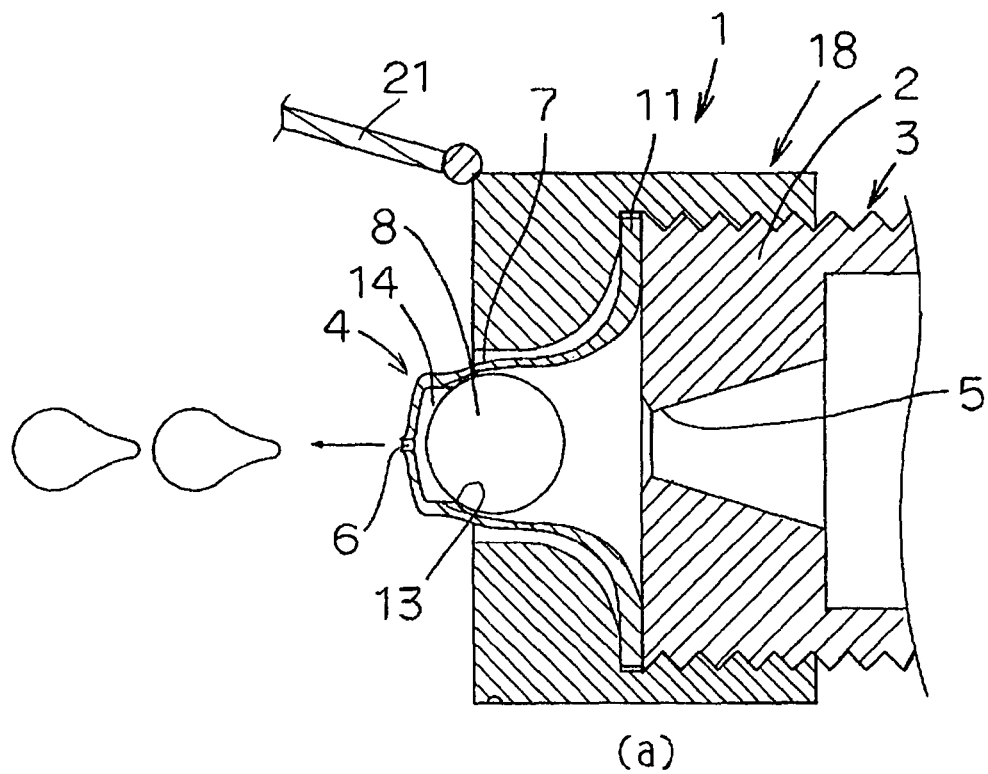
FIG. 13 shows a container and a backflow preventing plug according to an eighth embodiment, in which (a) is a vertical cross-sectional view showing a state in use, and (b) is a vertical cross-sectional view showing a state not in use.
Figure 13:
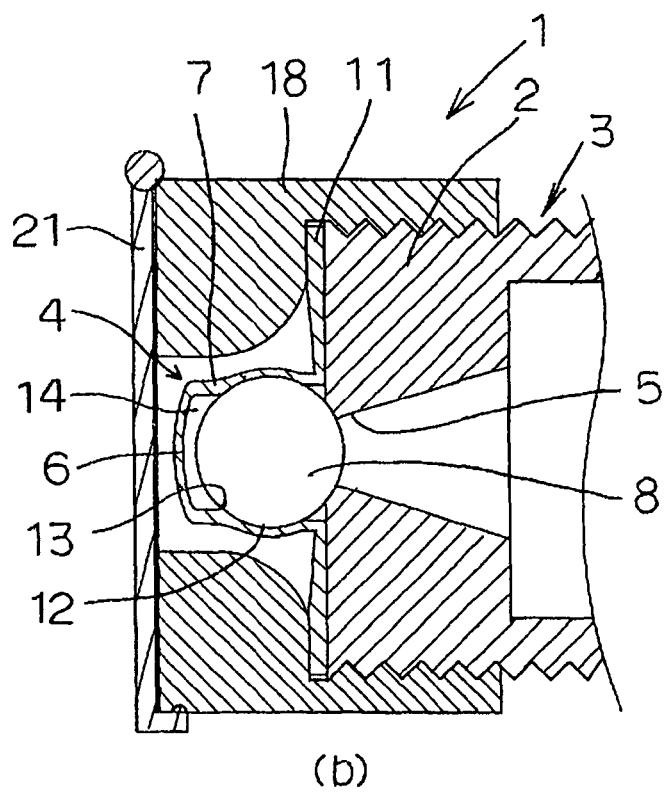

In an eighth embodiment shown in FIG. 13, the annular projection 15 is not formed on the resilient membrane 7 of the backflow preventing plug 4, which is a difference between this embodiment and the first embodiment. A container opening 5 is formed with an inclined surface which comes into direct tight contact with the plug member 8. The container 1 has a double-sealing structure including the sealing by a tight contact between the spherical sealing surface 12 of the plug member 8 of the backflow preventing plug 4 and the resilient membrane 7, and a sealing by a direct tight contact between the plug member 8 and the inclined surface. Other parts of the structure are substantially the same as the first embodiment, and the same effects are achieved.

Figure 14:
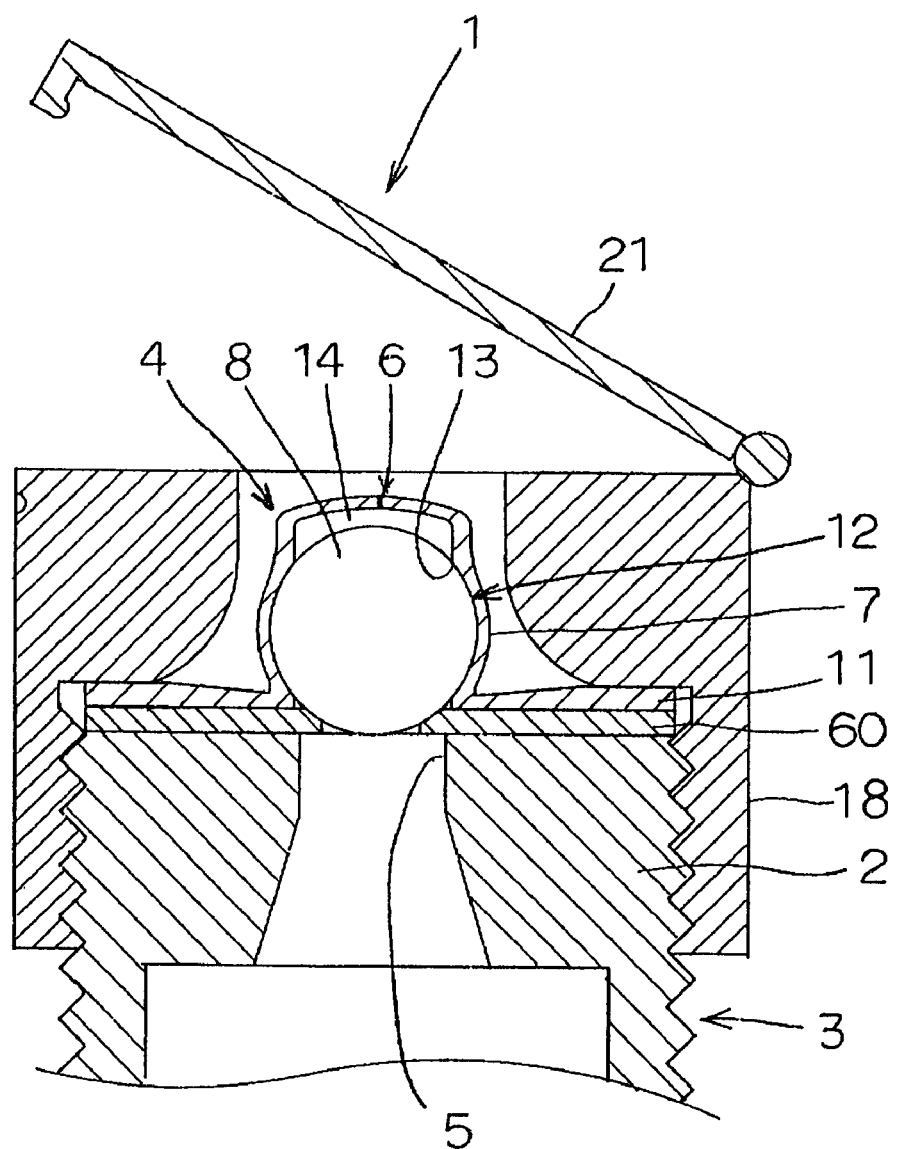
FIG. 14 is a vertical cross-sectional view showing a container and a backflow preventing plug according to a ninth embodiment.

A ninth embodiment shown in FIG. 14 is different from the first embodiment in that a sealing member 60 is provided between the flange of the resilient membrane 7 of the backflow preventing plug 4 and the front surface of the container body 3. The sealing member 60 has a disc shape and is formed of a resilient material having low oxygen permeability, such as butyl rubber or resilient resin. The sealing member 60 defines at the center thereof a hole for allowing contents to pass through, and when it is not in use, the plug member 8 comes into tight contact with the peripheral edge of the hole to close the hole. Specifically, the container 1 has a double-sealing structure including the sealing between the plug member 8 and the resilient membrane 7 through the spherical sealing surface 12, and a sealing between the plug member 8 and the sealing member 60. Other parts of the structure are substantially the same as the first embodiment, and the same effects are achieved.

Figure 15:
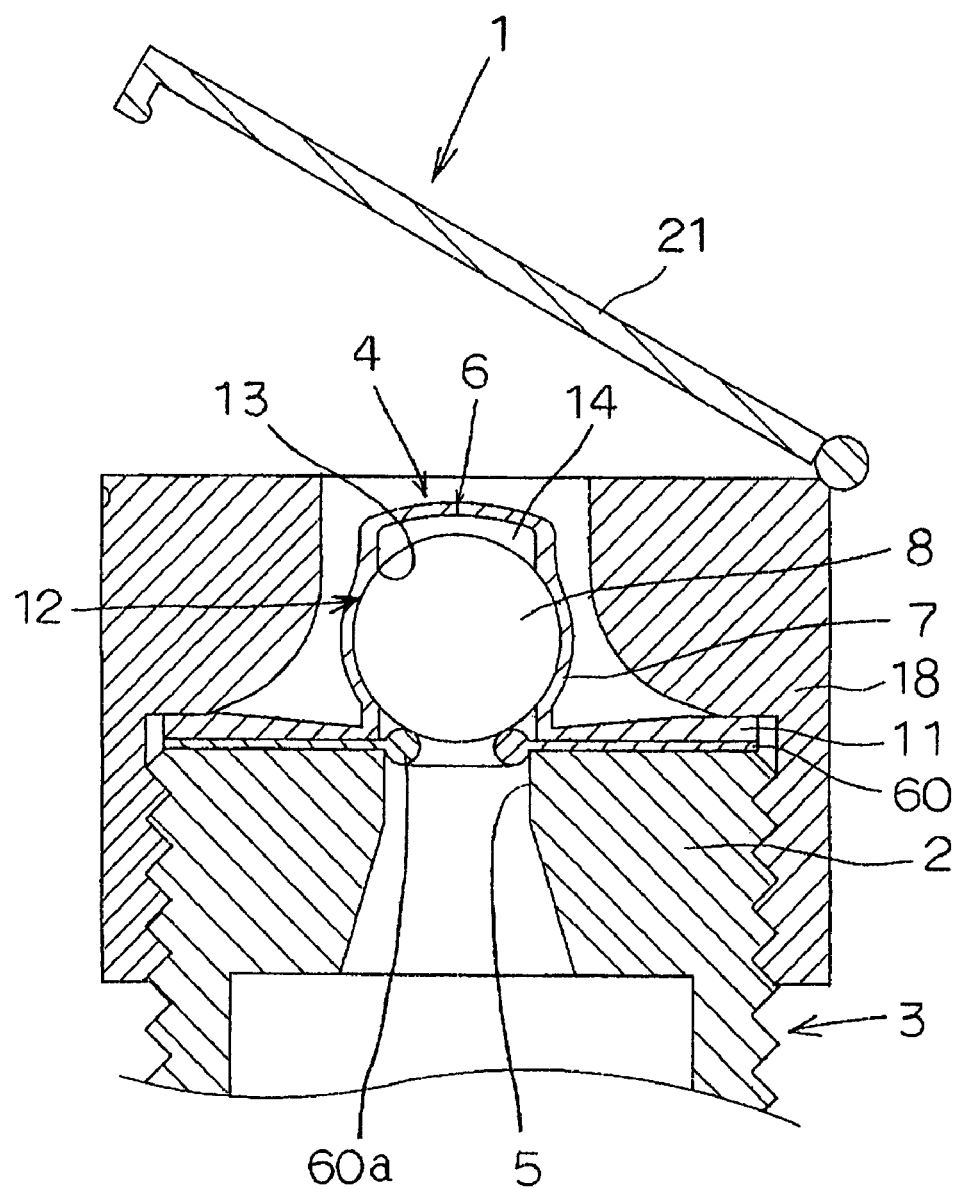
FIG. 15 is a vertical cross-sectional view showing a container and a backflow preventing plug according to a tenth embodiment.

The container 1 according to a tenth embodiment in FIG. 15 is different from the container 1 in the ninth embodiment in that a sealing portion (projection) 60a in an annular shape (doughnut shape) is formed along the peripheral edge of the hole on the sealing member 60. The annular sealing portion 60a has an advantage in that it engages the container opening for positioning the sealing member 60 without lateral displacement thereof. The container 1 has a double-sealing structure including the sealing by tight contact between the spherical sealing surface 12 of the plug member 8 and the resilient membrane 7, and a sealing by tight contact between the plug member 8 and the annular sealing portion 60a.

Figure 16:
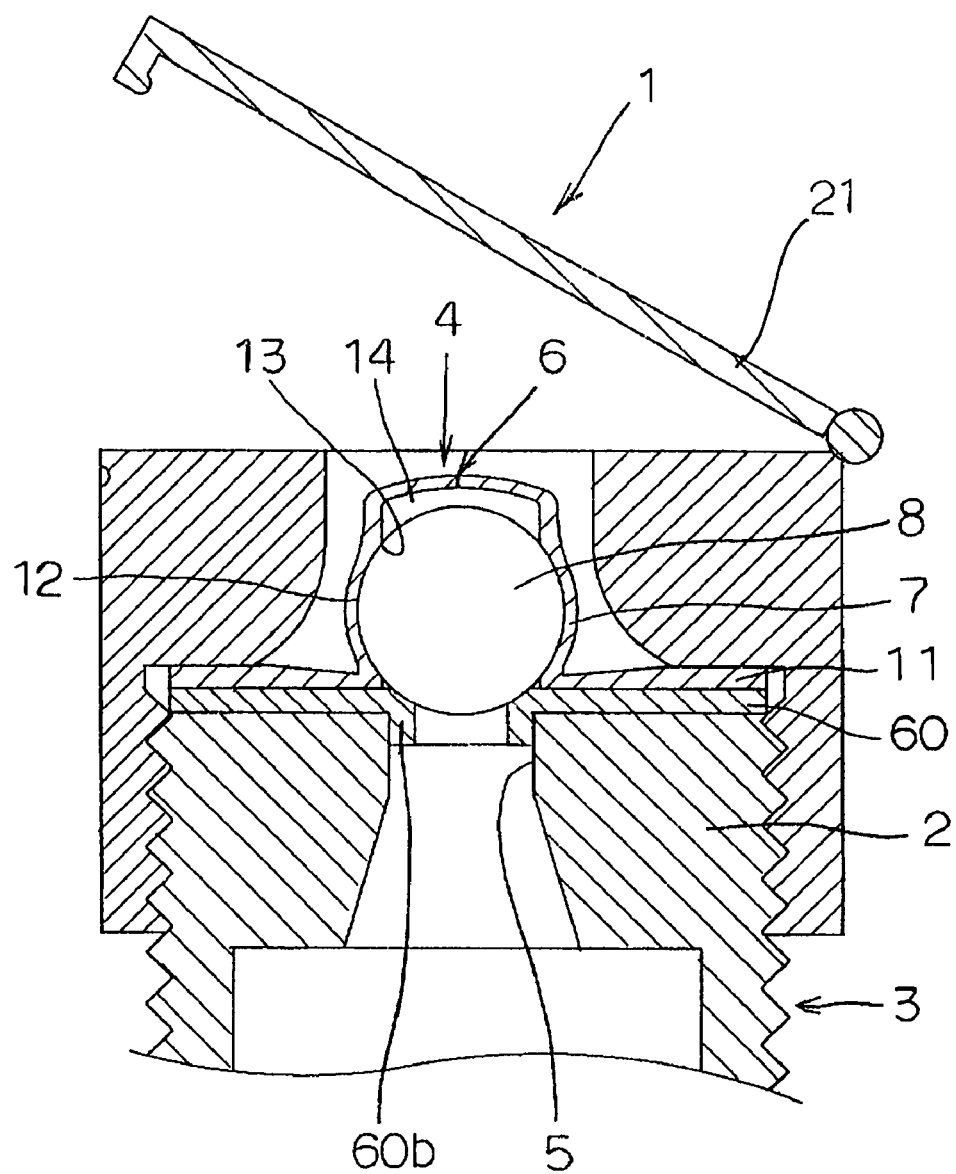
FIG. 16 is a vertical cross-sectional view showing a container and a backflow preventing plug 4 according to an eleventh embodiment.

The container 1 according to an eleventh embodiment shown in FIG. 16 is different from the container 1 according to the ninth embodiment shown in FIG. 14 in that this embodiment includes a cylindrical projection 60b formed along the peripheral edge of the hole of the sealing member 60 for allowing the contents to pass through as descried in the fifth embodiment.

The cylindrical projection 60b has a cylindrical shape projecting in the direction of the thickness of the plate-shaped sealing member 60. The distal end of the cylindrical projection 60b is opened, and hence the inner side of the cylindrical projection 60b defines a channel (flow path) for contents. Other parts of the structure are substantially the same as the container 1 in the ninth embodiment, and the same effects can be achieved.

As shown in FIG. 16, the cylindrical projection 60b projects toward the inside of the container body and is fitted into the discharge port 5 of the container opening 2. Accordingly, the sealing member 60 can be positioned reliably without lateral displacement, and reliable sealing with respect to the plug member 8 can be achieved. Although the container 1 shown in FIG. 13 to FIG. 16 is formed of an oxygen impermeable material, the resilient membrane 7 itself may be formed of a material having low oxygen permeability if the cost for such material is acceptable.

Figure 17:
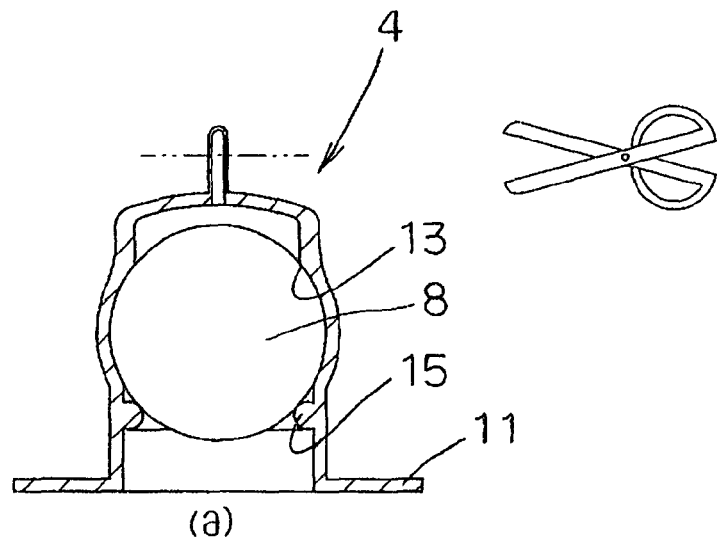
FIG. 17 shows a modification of the backflow preventing plug in vertical cross-sectional views.
Figure 17:
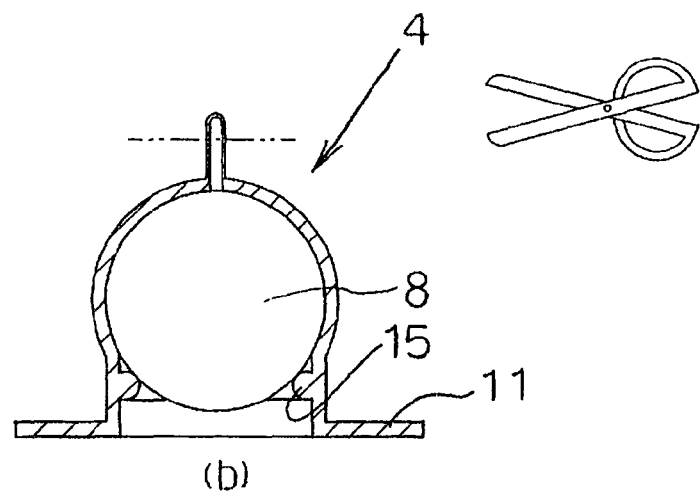
Figure 17:
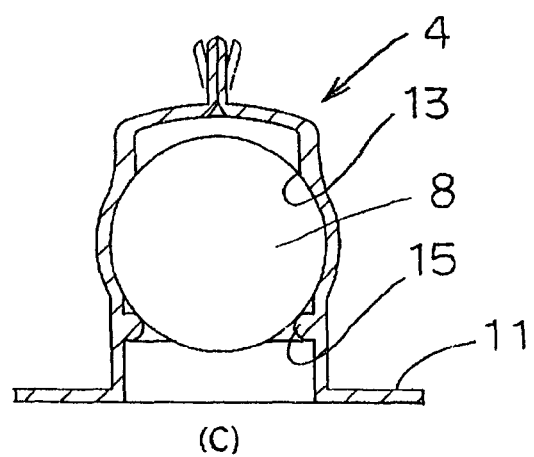

In the backflow preventing plug 4 in FIGS. 17(a), (b), irrespective of presence or absence of the clearance forming means 13, a tubular projection having a closed distal end is formed on the distal surface of the cylindrical portion of the resilient membrane 7 instead of the outlet port 6 of the backflow preventing plug 4. When using the container 1 provided with this backflow preventing plug 4, the body portion of the tubular projection is cut with scissors or the like, and a thus formed opening serves as the outlet port 6 for discharging contents therefrom. Other parts of the structure are substantially the same as the backflow preventing plug 4 in the first or other embodiments.

With this arrangement, for example, the backflow preventing plug 4 can prevent backflow of bacteria or outside air by its double-sealing structure as in the case of the first embodiment, and when the container 1 is circulated in the market as a container for a products, unauthorized usage or alteration of contents can be revealed easily by inspecting whether or not the tubular projection is cut off or not, which is advantageous.

In the backflow preventing plug 4 in FIG. 17(c), irrespective of the presence or absence of the clearance forming means 13, a bill-shaped projection which serves as the outlet port 6 is formed on the distal surface of the cylindrical portion of the resilient membrane 7 instead of the outlet port 6 of the backflow preventing plug 4. The projection is pressed outward and resiliently deformed by contents entering into the clearance between the plug member 8 and the resilient membrane 7 when the side surface of the container body 3 is pressed, so that the projection is opened to allow the contents to be discharged. Accordingly, for example, when pressing of the container body 3 is stopped, the bill-shaped projection is closed by its resilient restoring force to strongly block the discharge of contents.

Figure 18:
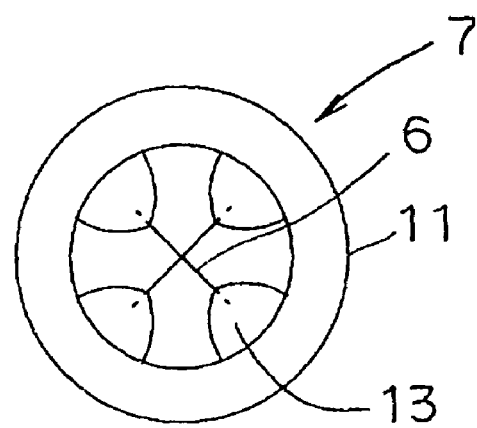
FIG. 18 shows a modification of the resilient membrane in bottom views.
Figure 18:
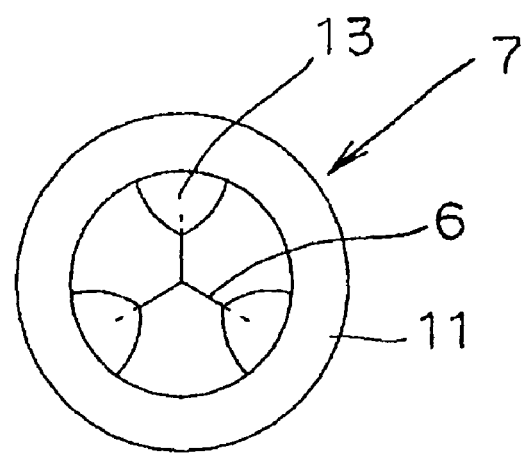

As shown in FIGS. 18(a), (b), a slit-shaped outlet port 6 is formed on the distal end of the resilient membrane 7, and end portions of the outlet port 6 are disposed at positions overlapping the projections serving as the clearance forming means 13, so that the end portions of the outlet port 6 (slit) can be prevented from being torn. Alternatively, the resilient membrane 7 may be formed to have an increased thickness at a position where the slit is formed as the outlet port 6, so that the slit is formed at the portion where the thickness is increased for preventing the end portion of the slit from being torn.

In addition to the structure shown in FIGS. 18(a), (b), it is also possible to provide a thickened portion on the outer surface of the distal end of the resilient membrane 7 and forming the outlet port 6 on the thickened portion for preventing the end portion of the slit as the outlet port 6 from being torn.

Table 1 shows a result of measurement of a backflow preventing capability for contents in the container 1 and in the backflow preventing plug 4 according to the present invention. In this measurement, a gauge pressure in the container body with respect to the atmospheric pressure is measured for a predetermined period (60 minutes).

TABLE 1

|  | Start 0 | 15 min. | 30 min. | 45 min. | 60 min. |
| --- | --- | --- | --- | --- | --- |
| 1st time | −0.038 | −0.038 | −0.038 | −0.038 | −0.038 |
| 2nd time | −0.042 | −0.042 | −0.042 | −0.042 | −0.042 |
| 3rd time | −0.040 | −0.040 | −0.040 | −0.040 | −0.040 |
| Average | −0.040 | −0.040 | −0.040 | −0.040 | −0.040 |

(unit: MPa, Temperature: 16° C.)

According to Table 1, the internal pressure of the container body 3 has changed little with the passage of time, and hence it is clear that the outside air is not flown back into the container 1.

Figure 19:
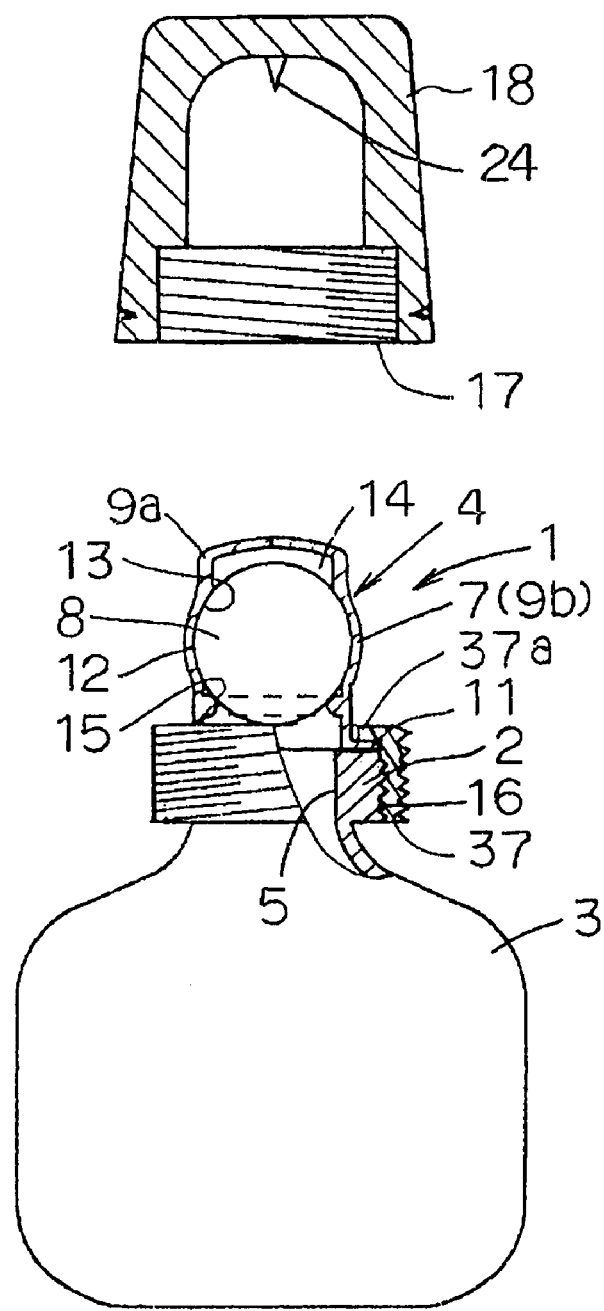
FIG. 19 is a side view of a container and a backflow preventing plug according to a twelfth embodiment.

In a twelfth embodiment shown in FIG. 19, a projection 24 with a sharp point for forming the outlet port 6 on the resilient membrane 7 is provided on the inner surface of the cap 18. The distal end of the backflow preventing plug 4 is not formed with the outlet port 6 in advance, and the outlet port 6 is formed by allowing the projection 24 to penetrate through the resilient membrane 7 when using the container 1. Accordingly, countermeasures for alteration of contents and perfect hermeticity before using the container 1 are secured, and contents can be preserved for a longer time.

Figure 20:
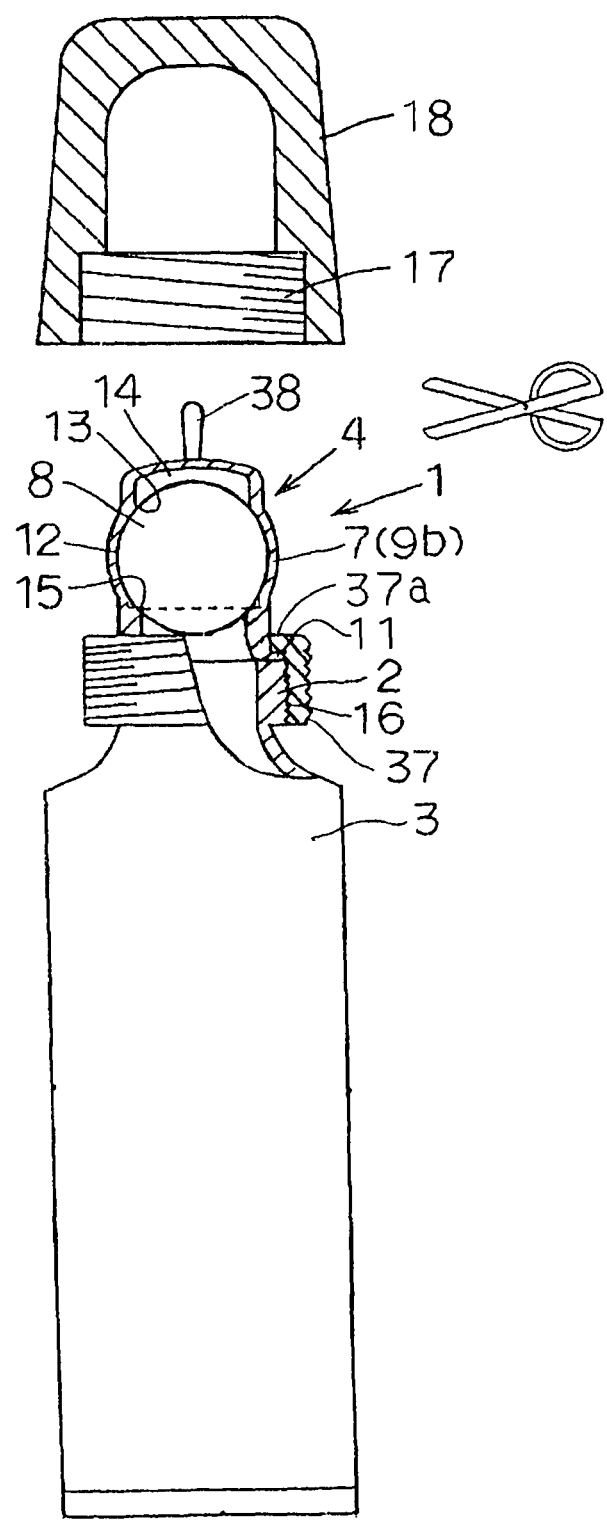
FIG. 20 is a side view of a container and a backflow preventing plug according to a thirteenth embodiment.

In a thirteenth embodiment shown in FIG. 20, the container 1 is formed with a pin 38, which is to be torn off or cut off when using the container 1 on the resilient membrane 7 at the distal end of the backflow preventing plug 4. Specifically, the pin 38 is torn off or cut off to form a hole or a slit as the outlet port 6 on the resilient membrane 7 when using the container 1. With such an arrangement as well, perfect hermeticity before using the container 1 is secured, and contents can be preserved for a longer time as in the case of the twelfth embodiment.

Figure 21:
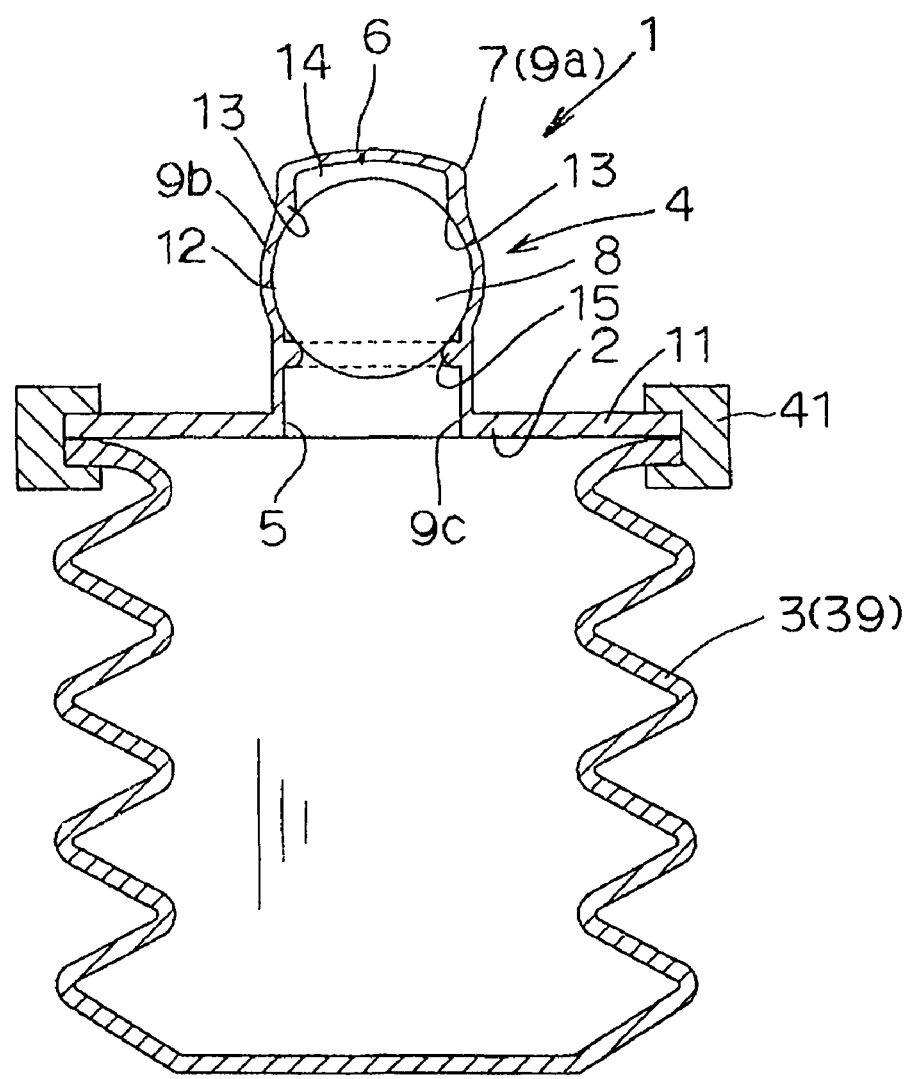
FIG. 21 is a vertical cross-sectional view of a container and a backflow preventing plug according to a fourteenth embodiment.

In a fourteenth embodiment shown in FIG. 21, the shape of the container body 3 is formed in an accordion shape. When using the container 1 by contractingly deforming the container body 3 in the content discharging direction so as to fold the container body 3, contents are discharged from the container opening 2 toward the backflow preventing plug 4 so as to be discharged from the outlet port of the backflow preventing plug 4.

Figure 22:
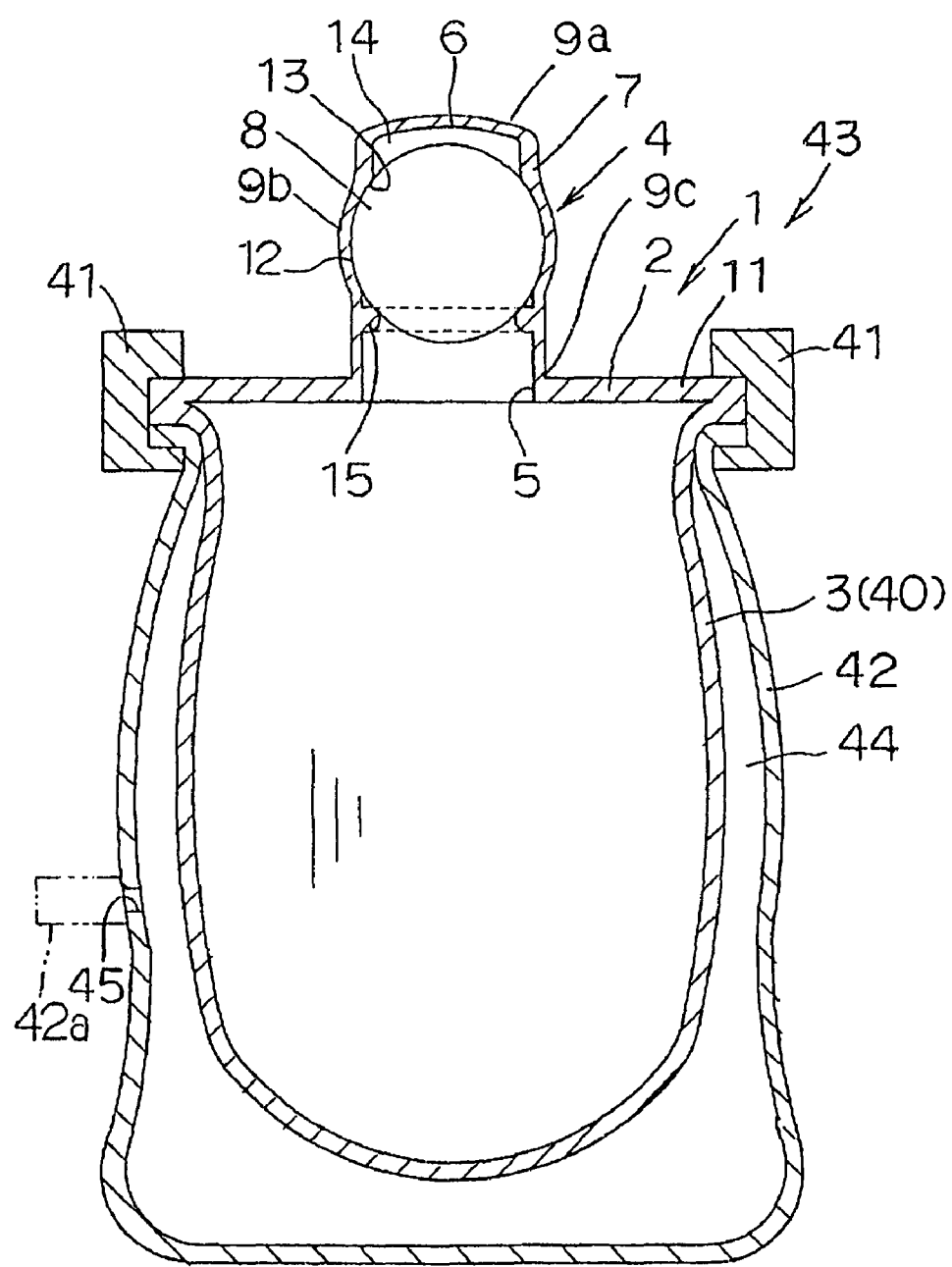
FIG. 22 is a vertical cross-sectional view showing a container, a backflow preventing plug, and a pouring device according to a fifteenth embodiment.

In a fifteenth embodiment shown in FIG. 22, the container body 3 of the container 1 is formed in a bag shape which is contractively deformable so as to discharge contents through the container opening 2, and an outer mantle 42 is provided outside the container body 3, so that the container 1 and the outer mantle 42 constitute a pouring device 43. The outer mantle 42 surrounds the container body 3 with a space therebetween so that the container body 3 is contractingly deformed by an external pressure (by squeezing by hand or the like) through air in the space.

The outer mangle 42 is formed of material such as plastic, and is capable of being deformed resiliently by finger pressure.

The outer mantle 42 has an opening attached to the fixture 41, and surrounds the container body 3 through an air layer. The outer mantle 42 is formed with an air hole 45 for communicating an air layer 44 therein and the outside.

Although the air hole 45 may be formed in advance on the outer mantle 42, for accommodating contents which may be easily affected by oxygen, it is also possible to adhere a seal on the air hole 45 to avoid circulation of air, or to integrally form a pin 42a for cutting off or tearing off the pin 38 to form the air hole 45 before use.

Alternatively, it is also applicable to form another air hole 45 separately from the aforementioned air hole 45 and provide a check valve at the air hole 45, so as to configure in such a manner that the outer mantle 42 is compressed with the air hole 45 closed with a finger but air can be introduced into the air layer 44 via the check valve without releasing the air hole 45, or to configure in such a manner that the check valve is provided on the air hole 45 itself so as to avoid the necessity to close the air hole 45 with a finger.

In the container 1, when the outer mantle 42 is compressed with the air hole 45 closed so as to contract the container body 3 through the air layer 44, contents are caused to outwardly expand the resilient membrane 7 in tight contact with the spherical sealing surface 12 to separate it from the spherical sealing surface 12 so as to pass by the plug member 8 to be discharged from the outlet port 6.

When the finger pressure of the outer mantle 42 is released after the contents are discharged, the outer mantle 42 tends to restore the original shape by its resilient restoring force, and since the container body 3 is contracted at this moment, air enters through the air hole 45 from outside so as to refill thus reduced capacity.

Entering of air into the air layer 44 in the outer mantle 42 maintains the container body 3 in the contracted state.

When the compression of the outer mantle 42 with the finger is stopped, since the internal pressure to expand the resilient membrane 7 is released, the expanded resilient membrane 7 comes into tight contact with the spherical sealing surface 12 again to perform sealing for preventing bacteria or outside air from coming into the container body 3.

For discharging contents next time, the aforementioned action is repeated. Since air for compensating the capacity reduced by the contracted container body 3 is replenished in the outer mantle 42, the outer mantle 42 is capable of performing the action to contract the container body 3 under substantially the same conditions.

When contents are sufficiently filled in the container body 3, it is also possible to compress the outer mantle 42 without closing the air hole 45 and apply finger pressure directly to the container body 3 through the outer mantle 42, so that the container body 3 is contracted.

Figure 23:
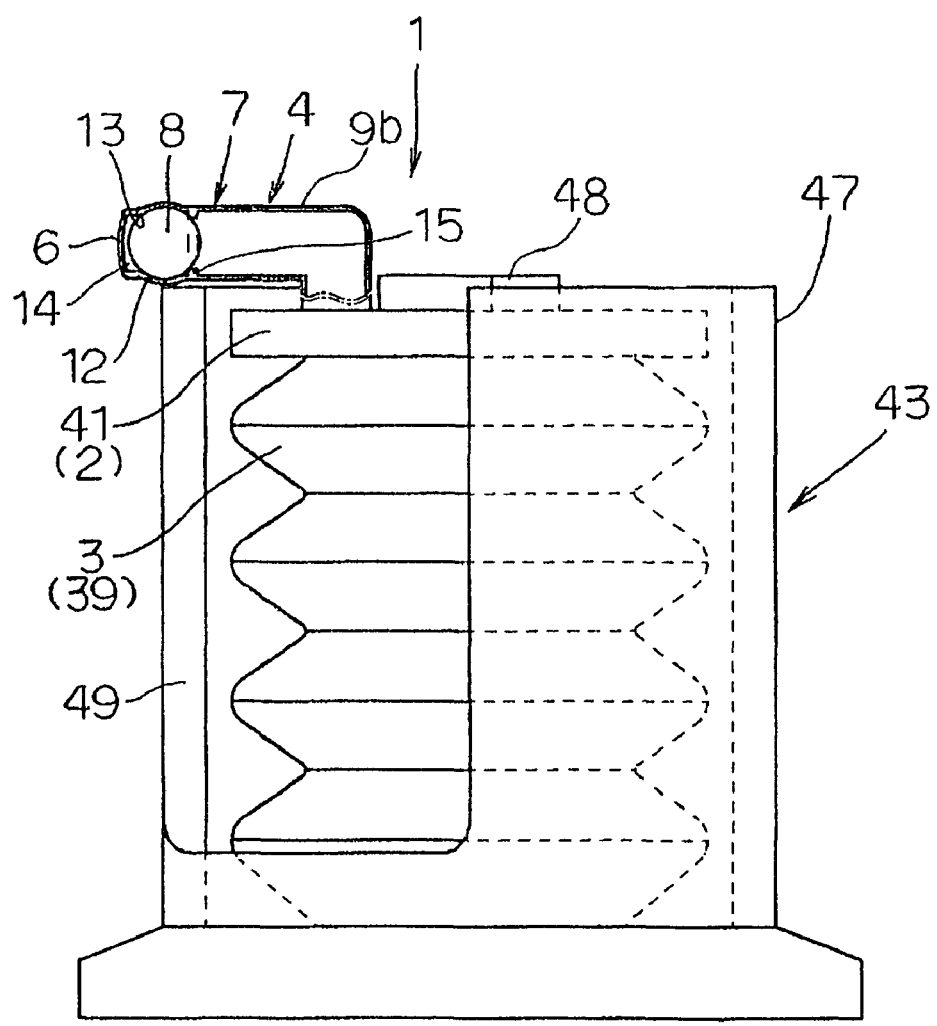
FIG. 23 is a side view of a container, a backflow preventing plug, and a pouring device according to a sixteenth embodiment.
Figure 24:
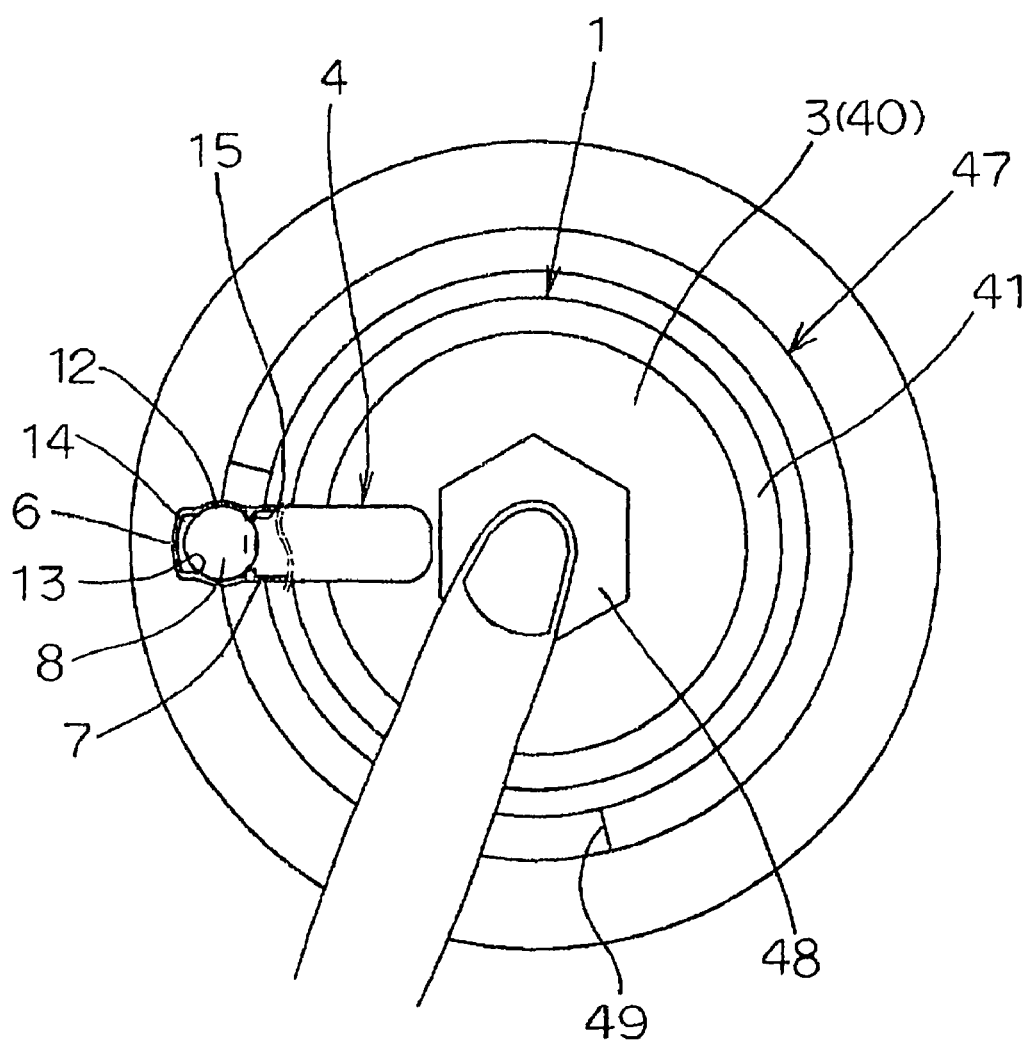
FIG. 24 is a plan view of the same.

In a sixteenth embodiment shown in FIG. 23 and FIG. 24, the pouring device 43 includes a container holder 47 for accommodating and retaining the container 1 provided with the container body 3 in an accordion shape, and allowing pressure application from the side of the container opening 2 for contractingly deforming the container body 3. The container 1 is a cartridge type, and the container 1 is replaceably accommodated in the container holder 47. Therefore, when contents in the container 1 are used up, since only the container 1 can be replaced, the container holder 47 can be reused.

On the upper surface of the container body 3, there is provided a push button 48 for downwardly contracting the container body 3. The body portion of the backflow preventing plug 4 is provided in the upper part of the container body 3 and formed in a bent shape so that the outlet port 6 is oriented to the lateral direction.

The container holder 47 includes a cylindrical portion for accommodating and holding the container 1 and a notch 49 formed on a part of the side wall of the cylindrical portion and extending from the upper opening to the bottom thereof so as not to obstruct downward movement of the backflow preventing plug 4 and a finger placed on the push button 48 when contracting the container 1 downward. In this arrangement, since contents can be discharged by pressing the container from above in a state in which the container 1 is accommodated and held in the container holder 47, the pouring device 43 facilitates handling of the container.

Figure 25:
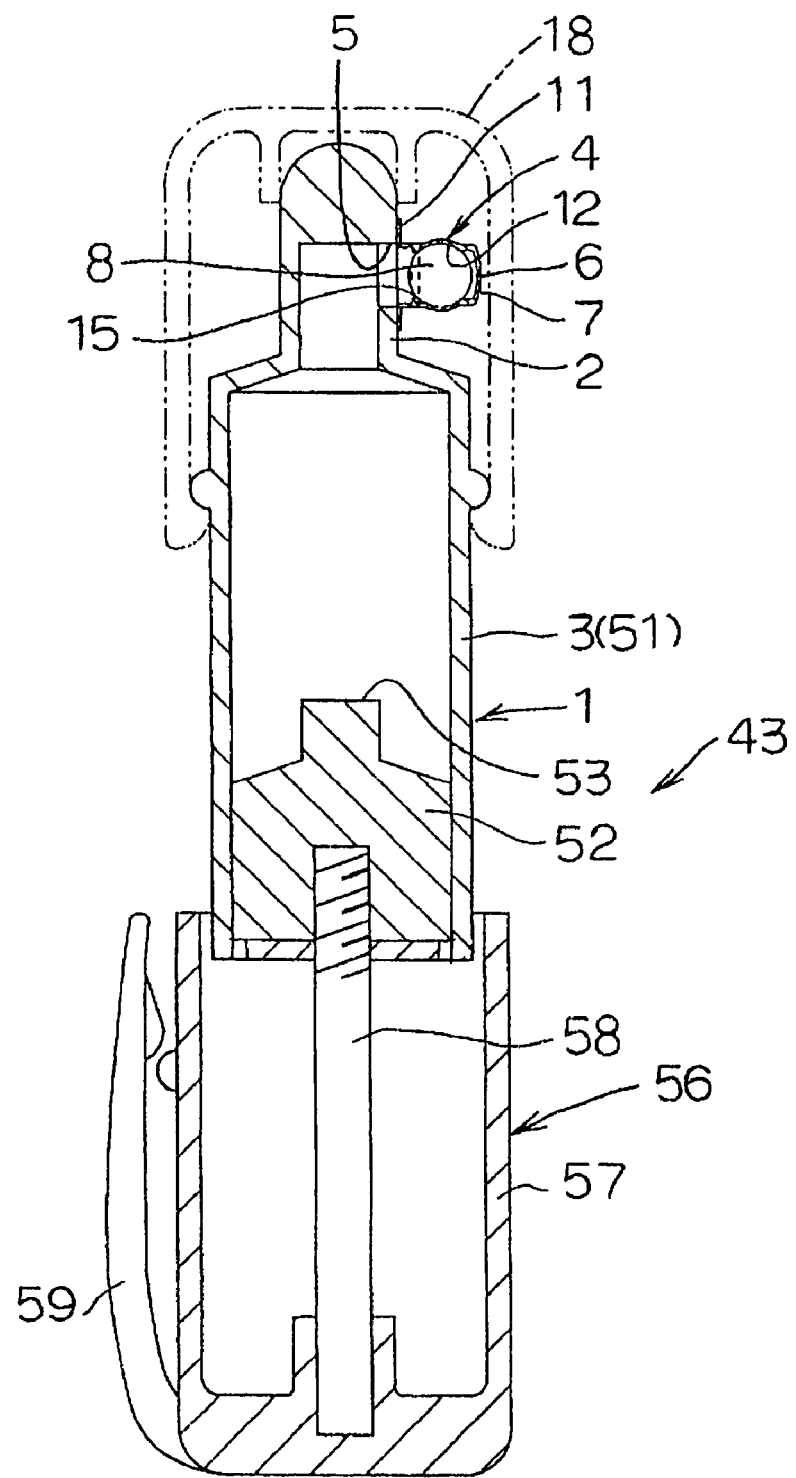
FIG. 25 is a vertical cross-sectional view of a container, a backflow preventing plug, and a pouring device according to a seventeenth embodiment.

In a seventeenth embodiment in FIG. 25, the container body 3 of the container 1 includes a cylindrical member 51 for storing contents, and a piston 52 axially slidably fitted into the cylindrical member 51. The distal end of the cylindrical member 51 is formed into a cylindrical shape having a smaller diameter than that of the body portion and has on the side wall thereof the backflow preventing plug 4 oriented in the lateral direction.

The piston 52 includes a column shaped body portion having a diameter slightly larger than that of the inner diameter of the body portion of the cylindrical member 51 and a column shaped projection 53 to be fitted to the distal end of the cylindrical member 51.

The container 1 is provided with a pushing member 56 on the rear portion thereof for pushing the piston 52 in the content discharging direction relative to the cylindrical member 51, the container 1 and the pressing member 56 are provided, and the container 1 and the pressing member 56 constitute the pouring device 43.

A clip 59 is provided on the outer surface of the pushing member 56, so that, for example, as in the case of a pen having a clip, the pouring device 43 can be retained on a pocket of a cloth by hooking the clip 59.

Figure 26:
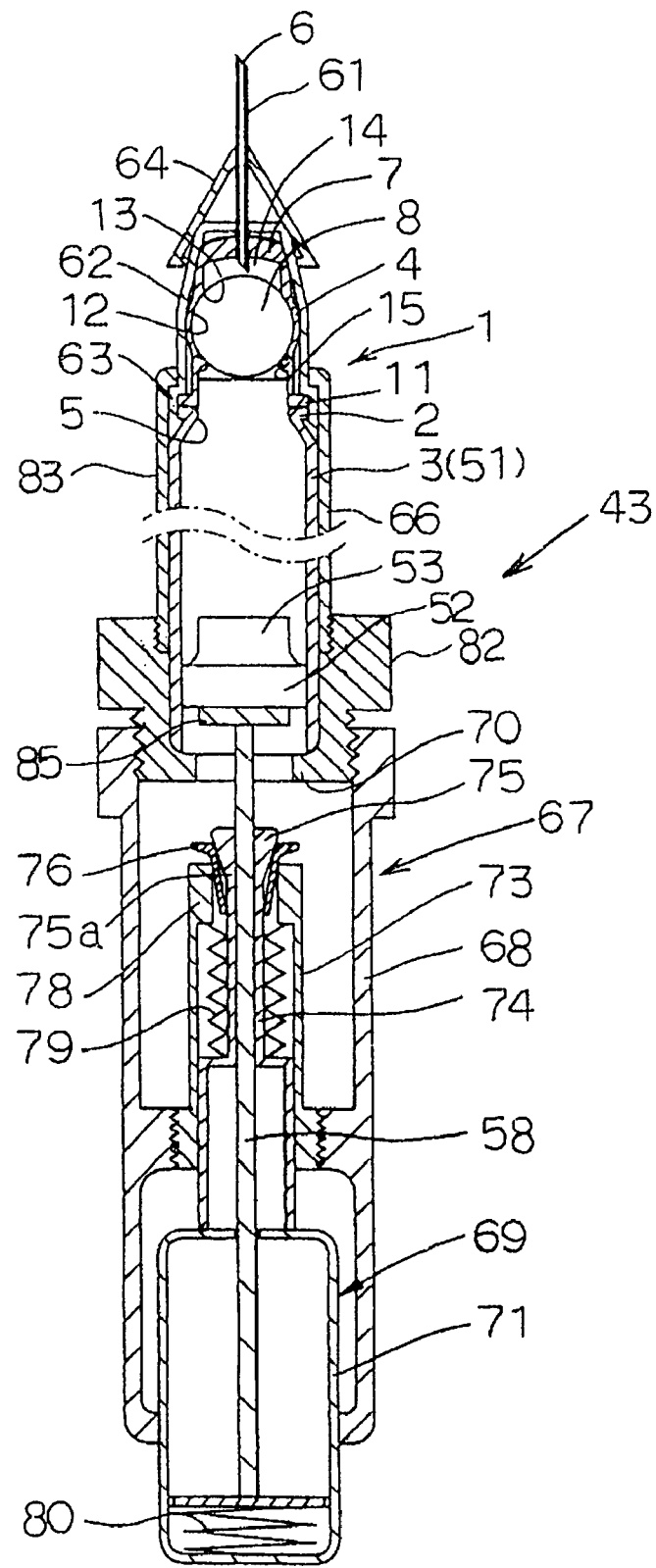
FIG. 26 is a vertical cross-sectional view of a container, a backflow preventing plug, and a pouring device according to an eighteenth embodiment.

In an eighteenth embodiment shown in FIG. 26, the container body 3 of the container 1 includes the cylindrical member 51 for storing contents, and the piston 52 axially slidably fitted to the cylindrical member 51. The cylindrical member 51 is formed in a cylindrical shape having the flange-shaped container opening 2 at the distal end thereof. The backflow preventing plug 4 is integrally formed with the container opening 2. The backflow preventing plug 4 is covered by an outlet port fitting 62 having a tubular needle 61 for discharging contents. The outlet port fitting 62 has a cylindrical shape and is provided at the proximal portion thereof with a fixture 63 for clamping and fixing the container opening 2 and the flange at the proximal portion of the backflow preventing plug 4 integrally. The container 1 is a cartridge type, and can be replaced. The cartridge type container 1 accommodates, for example, an injection. In this cartridge type structure, the thickness of the distal end of the resilient membrane 7 of the backflow preventing plug 4 where the needle is provided can be increased to achieve multiple usage of the injection.

On the distal side of the outlet port fitting 62, there is provided a conical holding portion 64 for holding the tubular needle 61, and the tubular needle 61 is projected from the top of the holding portion 64 toward the axial center of the container 1. The proximal end of the tubular needle 61 is passed through the resilient membrane 7 of the backflow preventing plug 4 and positioned in the backflow preventing plug 4. Contents are discharged from the outlet port at the distal end of the tubular needle 61 through the tubular needle 61.

The pouring device 43 includes a cartridge holder 66 for supporting the container 1 and a fixed quantity discharging mechanism 67 capable of pouring contents by a constant small amount by one pushing operation for discharging the contents from the container opening 2 by moving the piston 52 of the container 1 in the content discharging direction by a predetermined distance.

The fixed quantity discharging mechanism 67 employs a lead knocking-out mechanism for a mechanical pensile, in which an discharging mechanism body 68 is screwed onto a cartridge holder 66 (82, 83) for accommodating and retaining the container 1 so as to be capable of adjusting the amount of screwing, a knocking member 69 is inserted and supported in the discharging mechanism body 68 so as to be capable of moving in the axial direction, a pushing rod 58, which corresponds to a lead of the mechanical pensile, is inserted into the knocking member 69, and the distal end of the pushing rod 58 is connected to the piston 52 of the container body 3. The rear end of the cartridge holder 66 is positioned in the discharging mechanism body 68 to form an annular guiding portion 70.

The knocking member 69 has a three-step cylindrical shape in the axial direction comprising a large diameter cylindrical portion 71 on the rear end thereof which is slidably supported in the rear portion of the discharging mechanism body 68, a middle portion which is guided by a guiding holder 73 provided in the discharging mechanism body 68, and a small diameter portion 74 on the front end thereof which includes a tightening portion 75 having a slit on its distal end.

The tightening portion 75 is split into three (may be two or four) and capable of loosening or tightening the pushing rod 58, and the outer peripheral surface thereof is formed with a tapered surface 75a which increase in diameter as it approaches the distal end of the small diameter portion 74.

A squeezing member 76 formed in a tapered tube shape is fitted on the tightening portion 75. When the tightening portion 75 advances into the squeezing member 76, the tightening portion 75 is squeezed so as to clamp the pushing rod 58.

The squeezing member 76 is capable of coming into abutment with the guiding portion 70 by advancing forward. When it abuts against the guiding portion 70, the movement thereof is blocked and hence only the tightening portion 75 advances. Accordingly, fitted relation between the tightening portion 75 and the squeezing member 76 is released, and the clamping of the pushing rod 58 by the tightening portion 75 is released.

The guiding holder 73 disposed in the discharging mechanism body 68 is formed with a receiving portion 78 on the distal end thereof for preventing rearward movement of the squeezing member 76 and allowing the tightening portion 75 to enter into the squeezing member 76. Between the receiving portion 78 of the guiding holder 73 and the middle portion of the knocking member 69, there is disposed a return spring 79.

In the large diameter cylindrical portion 71 of the knocking member 69, a balance spring 80 is provided for urging the pushing rod 58 softly toward the container 1.

In the fixed quantity discharging mechanism 67 arranged as described above, the pushing rod 58 of the piston 52 is moved to the rear end position in a state in which the container 1 is accommodated and retained in the cartridge holder 66, the balance spring 80 is compressed, and the knocking member 69 is moved to the rear end position by the return spring 79.

From this state, when the discharging mechanism body 68 is held and the knocking member 69 is pressed once with a finger or the like, the tightening portion 75 clamping the pushing rod 58 with the squeezing member 76 advances with the pushing rod 58 clamped and moves the pushing rod 58 and the piston 52 by a certain distance, so that a fixed quantity of contents are discharged from the outlet port 6.

When the squeezing member 76 abuts against the guiding portion 70 in the course of pressing the knocking member 69, fitted state of the squeezing member with respect to the tightening portion 75 is released. Accordingly, since the tightening portion 75 is released from constriction on the outer periphery thereof and, hence, is loosened, the tightening portion releases the pushing rod 58 which has been clamped.

Accordingly, the pushing rod 58 and the piston 52 are stopped at positions where they are advanced by a certain distance. When the pressing of the knocking member 69 is released thereafter, the tightening portion 75 of the knocking member 69 is moved to the rear end position by the return spring 79 without clamping the pushing rod 58.

In the latter half of the returning movement of the knocking member 69, the squeezing member 76 enters into the receiving portion 78 of the guiding holder 73 so that the movement thereof is constricted, and the tightening portion 75 enters into the squeezing member 76 and clamps the pushing rod 58.

By adjusting the distance between the guiding portion 70 and the guiding holder 73, the amount of movement of the piston 52 by one pressing of the knocking member 69 can be adjusted. Also, a spacer may be interposed in the clearance between the discharging mechanism body 68 and a first holder member 82 and fixed so as not to move for adjusting the amount of movement.

Figure 27:
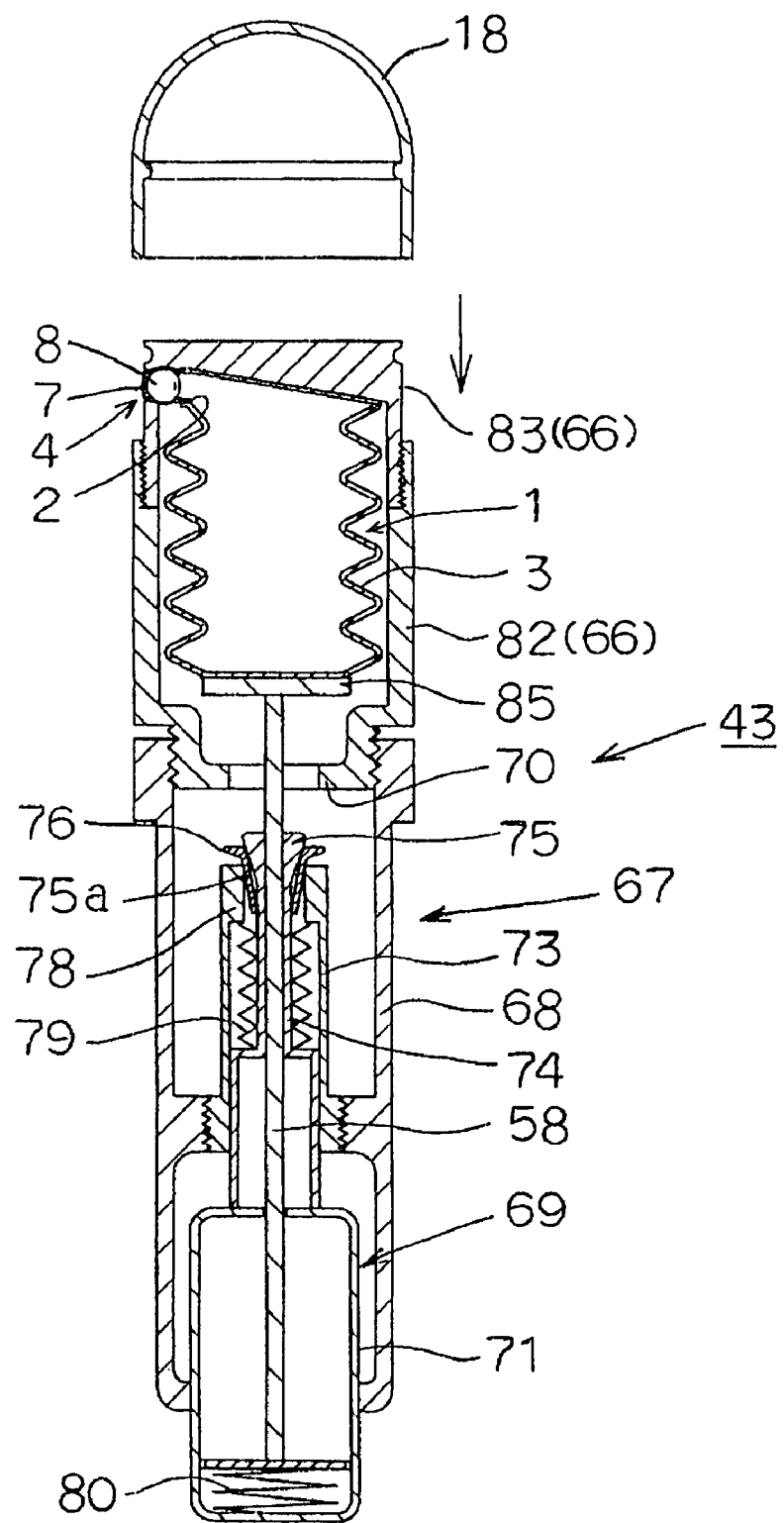
FIG. 27 is a vertical cross-sectional view of a container, a backflow preventing plug, and a pouring device according to a nineteenth embodiment.

In a nineteenth embodiment shown in FIG. 27, the cartridge container 1 having the accordion shaped container body 3 which is contractively deformable is used, and the pouring device 43 includes the cartridge holder 66 for supporting the container 1, and the fixed quantity discharging mechanism 67 described in the eighteenth embodiment. The cartridge holder 66 includes a cylindrical first holder member 82 having the annular guiding portion 70, and a cylindrical second holder member 83 fitted to the first holder member 82 for holding the container 1 from above. The first holder member 82 and the second holder member 83 are joined by screwing or the like. At the distal end of the pushing rod 58 of the fixed quantity discharging mechanism 67, there is provided a supporting plate 85 for supporting the container 1 by abutting against the outer surface of the bottom of the container 1, and the supporting plate 85 contracts the container 1 by folding the same by the movement of the pushing rod 58 caused by the pushing movement of the fixed quantity discharging mechanism 67 described in the eighteenth embodiment.

Figure 28:
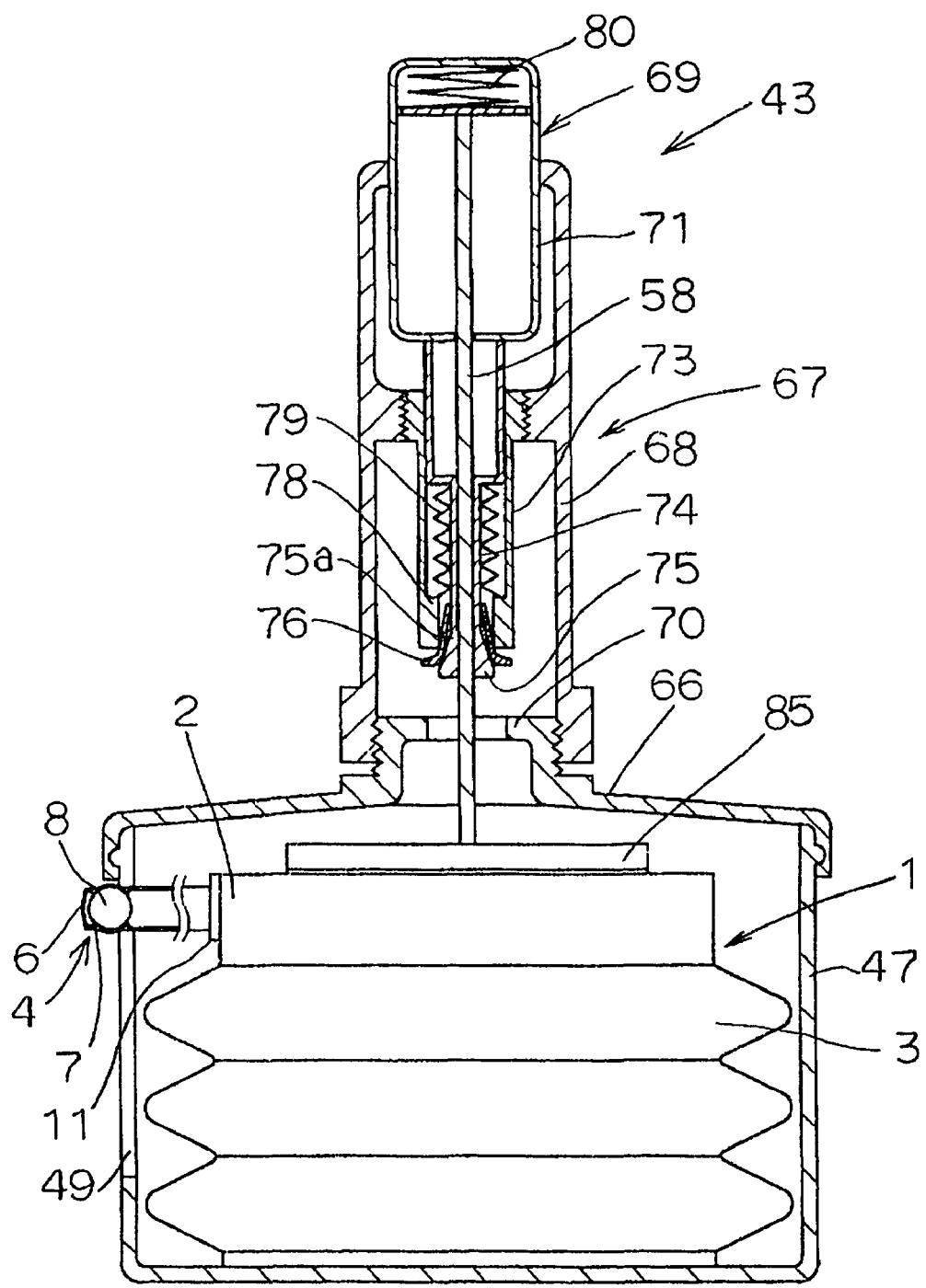
FIG. 28 is a vertical cross-sectional view showing a container, a backflow preventing plug, and a pouring device according to a twentieth embodiment.
Figure 29:
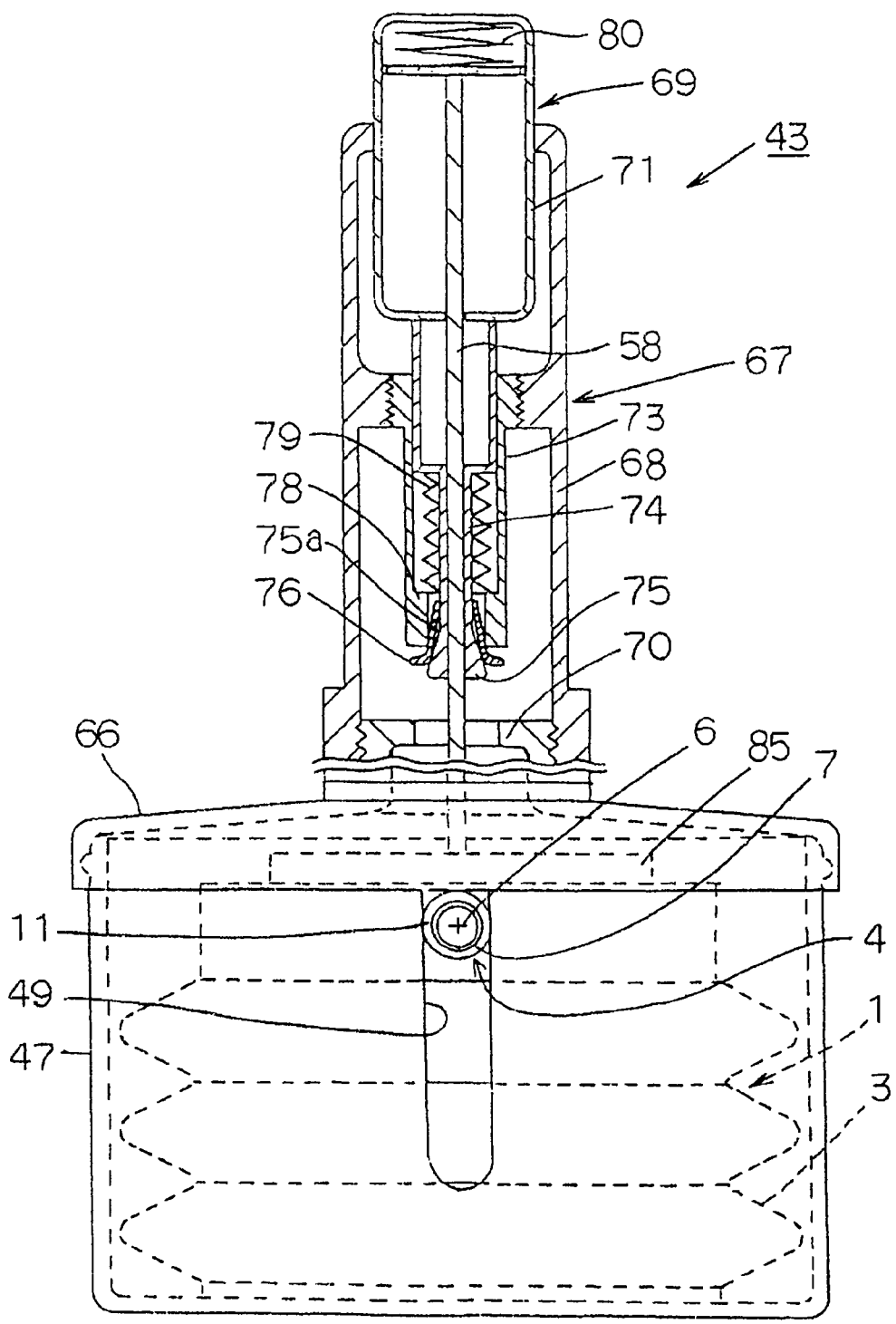
FIG. 29 is a side view of the same.

In a twentieth embodiment shown in FIG. 28 and FIG. 29, the container 1 is provided with the accordion shaped contractively deformable container body 3, and the backflow preventing plug 4 projecting from the upper side wall of the container body 3 in the lateral direction.

In the pouring device 43, the cartridge container 1 is stored in the container holder 47 having the notch 49 as described in the sixteenth embodiment, and the upper portion of the container holder 47 is closed by the cylindrical cartridge holder 66 formed integrally with the fixed quantity discharging mechanism 67 described in the eighteenth embodiment.

In the container and the pouring device 43 in the twelfth embodiment to the twenties embodiment, although the backflow preventing plug 4 according to the first embodiment is provided, the backflow preventing plug 4 according to the second embodiment to the eleventh embodiment is also applicable.

It should be noted that the present invention is not limited to the embodiment described above, and variations or modifications as described below are included in the present invention. In the backflow preventing plug 4 according to the first embodiment, the number of projections formed as the clearance forming means 13 is not limited to four, but may be one to three or five or more. Various shapes of the container body 3 may be employed, such as the shape of a bag for pouches or of a folded paper bag, and material thereof may be biodegradable plastic, water-proof paper, synthetic resin, rubber, metal such as aluminum. Material of the plug member 8 is not limited to hard resin, but may be various resin material, rubber, stone, glass, ceramic, shell, wood, metal, or antibacterial material including silver plating or the like. Alternatively, the plug member 8 may be coated with antibacterial or bactericidal metal such as silver.

Although the body portion 9b of the resilient membrane 7 is formed into a cylindrical shape in the first embodiment, the body portion 9b may be formed into a tapered cylindrical shape tapered toward the distal end 9a thereof. In this case, an increased resilient force (resilient restoring force) of the resilient membrane 7 in the direction from the distal end 9a toward the opening 9c is applied to the plug member 8 retained in the resilient membrane 7. Therefore, when the plug member 8 is pressed against the annular projection 15 by thus increased resilient force, tight contact between the plug member 8 and the annular projection 15 increases, and hence further reliable sealing is advantageously achieved.

INDUSTRIAL APPLICABILITY

The present invention is effective for the plug, the container, and the pouring device for preventing oxidization of contents.

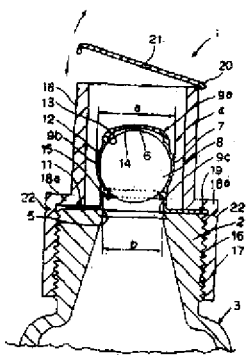

The invention claimed is:

1. A backflow preventing plug including a thin film resilient membrane defining a flow path and forming an intake port and an outlet port of the flow path,
a ball-shaped plug member which is retained by the resilient membrane between the intake port and the outlet port and which is formed with a spherical sealing surface for restricting flow of fluid by coming into resilient contact with a middle portion of the resilient membrane; and
clearance forming means comprising at least one of the following:
a plurality of projection portions each of which has a shape of projection
and which are located at such positions on an inner surface of the resilient membrane as to be closer to the outlet port than to a center of the ball-shaped plug member and to be apart from each other and substantially symmetrically located about a circumferential surface of the ball-shaped plug member;
a plurality of projections extending from an outer surface of the ball-shaped plug member toward the resilient membrane, said projections being closer to the outlet port than to a center of the ball-shaped plug member and to be apart from each other and substantially symmetrically located about a circumferential surface of the ball-shaped plug member; and
a plurality of recesses formed in a recess shape which are located at such positions on the plug member as to be closer to the outlet port than to a center of the ball-shaped plug member and be apart from each other and substantially symmetrically located about a circumferential surface of the ball-shaped plug member and which communicate with each other at closest positions to the outlet port,
wherein said clearance forming means forms a clearance between the outlet port and the plug member, and said resilient membrane is expanded and deformed in a direction away from said plug member by a pressure applied from the intake port.

2. A backflow preventing plug according to claim 1, characterized in that said resilient membrane is formed of an elastic rubber member.

3. A backflow preventing plug according to claim 1, characterized in that the plug member has a spherical shape.

4. A backflow preventing plug according to claim 1, characterized in that the plug member has an ellipsoidal shape.

5. A backflow preventing plug according to claim 1, characterized in that the outlet port is formed in a slit-shape.

6. A backflow preventing plug according to claim 1, characterized by further comprising discharge guiding means for guiding contents passing through the flow path with expanding the resilient membrane by an increase in fluid pressure on the intake port side toward the outlet port.

7. A container, comprising:
the backflow preventing plug according to claim 1 and a container body having an opening,
wherein the backflow preventing plug is attached to the container opening.

8. A container according to claim 7 characterized by comprising fixed quantity discharging means for allowing contents to be discharged by a fixed quantity.

9. A container according to claim 7 characterized in that the container body is formed in a contractively deformable bag shape for discharging contents from the container opening.

10. A container according to claim 8 characterized in that the container body is formed in a contractively deformable bag shape for discharging contents from the container opening.

11. A container according to claim 7 characterized in that the container body is formed in a contractively deformable accordion shape for discharging contents from the container opening.

12. A container according to claim 8 characterized in that the container body is formed in a contractively deformable accordion shape for discharging contents from the container opening.

13. A container according to claim 7 characterized in that the container body includes a cylindrical member for accommodating contents, and an axially slidable piston fitted into the cylindrical member.

14. A container according to claim 8 characterized in that the container body includes a cylindrical member for accommodating contents, and an axially slidable piston fitted into the cylindrical member.

15. A pouring device comprising the container according to claim 9; and
an outer mantle surrounding the container body of said container through a space therebetween, the outer mantle being resiliently deformable so as to contractingly deform the container body through air in the space by a resilient deformation thereof due to an external pressure.

16. A pouring device comprising the container according to claim 10; and
an outer mantle surrounding the container body of said container through a space therebetween, the outer mantle being resiliently deformable so as to contractingly deform the container body through air in the space by a resilient deformation thereof due to an external pressure.

17. A pouring device comprising the container according to claim 11; and
a container holder for holding said container and allowing the container body to be pressurized from the container opening side for contracting deformation.

18. A pouring device comprising the container according to claim 12; and
ner holder for holding said container and allowing the container body to be pressurized from the container opening side for contracting deformation.

19. A pouring device comprising the container according to claim 13; and
dge holder for supporting said container, and a fixed quantity discharging mechanism for causing contents to be poured by a predetermined small amount at every pushing operation for discharging the contents from the container opening of the container.

20. A pouring device comprising the container of claim 13; and
a pushing member for pushing the piston with respect to the cylindrical member of said container in a content discharging direction.

21. A pouring device comprising the container of claim 14; and
a pushing member for pushing the piston with respect to the cylindrical member of said container in a content discharging direction.

22. The backflow preventing plug of claim 1, wherein the ball-shaped plug member is always retained by the resilient membrane between the intake port and the outlet port.

23. A backflow preventing plug including a thin film resilient membrane defining a flow path and forming an intake port and an outlet port of the flow path,
a ball-shaped plug member which is retained by the resilient membrane between the intake port and the outlet port and which is formed with a spherical sealing surface for restricting flow of fluid by coming into resilient contact with a middle portion of the resilient membrane; and
clearance forming means forming a clearance between the outlet port and the ball-shaped plug member, comprising at least one of the following:
a plurality of projections each of which has a shape of projection and which are located at such positions on an inner surface of the resilient membrane as to be closer to the outlet port than to a center of the ball-shaped plug member and to be apart from each other in a circumferential direction at substantially equal distances from the center of the ball-shaped plug member;
a plurality of projections extending from an outer surface of the ball-shaped plug member toward the resilient membrane, said projections being closer to the outlet port than to a center of the ball-shaped plug member and to be apart from each other in a circumferential direction at substantially equal distances from the center of the ball-shaped plug member; and
a plurality of recesses formed in a recess shape which are located at such positions on the plug member as to be closer to the outlet port than to a center of the ball-shaped plug member and be apart from each other in a circumferential direction at substantially equal distances from the center of the ball-shaped plug member and which communicate with each other at closest positions to the outlet port,
wherein said clearance forming means forms a clearance between the outlet port and the plug member, and said resilient membrane is expanded and deformed in a direction away from said plug member by a fluid pressure applied from the intake port.

* * * * *

UNITED STATES PATENT AND TRADEMARK OFFICE
CERTIFICATE OF CORRECTION

| | | |
|---|---|---|
| PATENT NO. | : 8,042,714 B2 | Page 1 of 2 |
| APPLICATION NO. | : 10/526368 | |
| DATED | : October 25, 2011 | |
| INVENTOR(S) | : Masayasu Miyazaki et al. | |

It is certified that error appears in the above-identified patent and that said Letters Patent is hereby corrected as shown below:

Title page should be deleted and substitute therefor the attached title page

In the Drawings, sheet 1 of 29, consisting of Fig. 1, should be deleted and replaced with the following corrected Fig. 1:

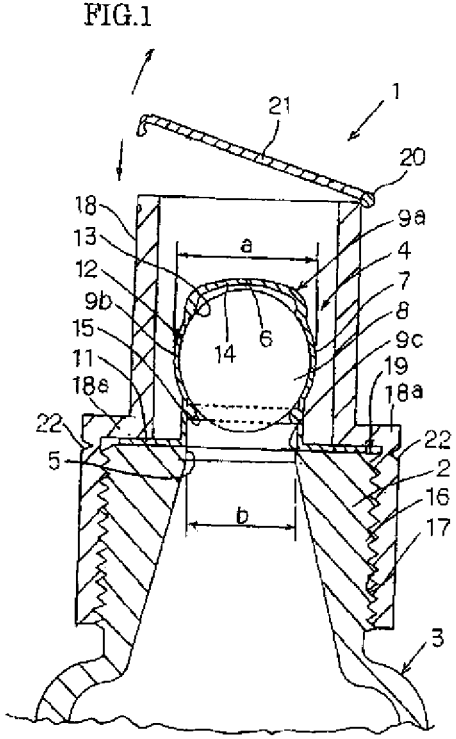

Signed and Sealed this
Twenty-seventh Day of December, 2011

David J. Kappos
*Director of the United States Patent and Trademark Office*

CERTIFICATE OF CORRECTION (continued)

(12) United States Patent
Miyazaki et al.

(10) Patent No.: US 8,042,714 B2
(45) Date of Patent: Oct. 25, 2011

(54) REVERSE-FLOW PREVENTION PLUG FOR CONTAINER, THE CONTAINER, AND POURING DEVICE

(75) Inventors: Masayasu Miyazaki, Yokohama (JP); Manabu Ikuta, Sakai (JP)

(73) Assignee: Sumitomo Rubber Industries, Ltd., Kobe (JP)

( * ) Notice: Subject to any disclaimer, the term of this patent is extended or adjusted under 35 U.S.C. 154(b) by 1719 days.

(21) Appl. No.: 10/526,368

(22) PCT Filed: Aug. 14, 2003

(86) PCT No.: PCT/JP03/10365
§ 371 (c)(1),
(2), (4) Date: Oct. 5, 2005

(87) PCT Pub. No.: WO2004/022444
PCT Pub. Date: Mar. 18, 2004

(65) Prior Publication Data
US 2006/0065673 A1    Mar. 30, 2006

(30) Foreign Application Priority Data

Sep. 6, 2002  (JP) .................... 2002-261891
May 15, 2003  (JP) .................... 2003-137579

(51) Int. Cl.
*B65D 5/72*     (2006.01)
(52) U.S. Cl. ........ 222/494; 222/105; 222/212; 222/213; 222/386; 222/386.5; 222/491
(58) Field of Classification Search ............ 222/94–96, 222/105, 206, 209, 212–215, 490–491, 494, 222/386.5, 386
See application file for complete search history.

(56) References Cited

U.S. PATENT DOCUMENTS

| | | | | |
|---|---|---|---|---|
| 1,987,156 A | * | 1/1935 | Paparello | 222/494 |
| 3,111,703 A | * | 11/1963 | Kaufman | 401/214 |
| 3,179,300 A | | 4/1965 | Davidson | |
| 4,342,522 A | * | 8/1982 | Mackles | 401/214 |
| 4,846,810 A | | 7/1989 | Gerber | |
| 5,005,732 A | | 4/1991 | Penn | |
| 5,033,647 A | * | 7/1991 | Smith et al. | 222/94 |
| 5,305,786 A | * | 4/1994 | Debush | 137/512.3 |

(Continued)

FOREIGN PATENT DOCUMENTS

JP       49-97245 A      8/1974

(Continued)

*Primary Examiner* — Frederick C. Nicolas
(74) *Attorney, Agent, or Firm* — Birch, Stewart, Kolasch and Birch LLP

(57) ABSTRACT

A backflow preventing plug, a container, and a pouring device in which a container body and a plug member are provided separately in a simple shape, and tight-contact property between the plug member and a resilient member is enhanced to improve a backflow preventing function are provided.
A backflow-preventing plug includes a resilient membrane formed of a thin film for defining a flow path having an inlet port and an outlet port, and a ball-shaped plug member retained in the flow path of the resilient membrane and formed with a spherical sealing surface for restricting fluid flow by coming into tight resilient contact with a middle portion of the resilient membrane. In a container, the backflow preventing plug is attached to a container opening of a container body accommodating contents. A pouring device includes, for example, a container holder accommodating and holding the container and allowing the container body to be pressurized from the container opening side to be contractingly deformed.

23 Claims, 29 Drawing Sheets